United States Patent
Meng et al.

(10) Patent No.: US 10,669,273 B2
(45) Date of Patent: Jun. 2, 2020

(54) USE OF AZA-TRYPTANTHRIN DERIVATIVES AS INHIBITORS OF IDO1 AND/OR TDO

(71) Applicant: Peking University, Beijing (CN)

(72) Inventors: Xiangbao Meng, Beijing (CN); Yu Chen, Beijing (CN); Zhongjun Li, Beijing (CN); Dongbo Lu, Beijing (CN); Meiqi Zhang, Beijing (CN)

(73) Assignee: Peking University, Beijing (CN)

( * ) Notice: Subject to any disclaimer, the term of this patent is extended or adjusted under 35 U.S.C. 154(b) by 0 days.

(21) Appl. No.: 16/090,486

(22) PCT Filed: Apr. 1, 2017

(86) PCT No.: PCT/CN2017/079371
§ 371 (c)(1),
(2) Date: Oct. 1, 2018

(87) PCT Pub. No.: WO2017/173973
PCT Pub. Date: Oct. 12, 2017

(65) Prior Publication Data
US 2019/0112308 A1 Apr. 18, 2019

(30) Foreign Application Priority Data
Apr. 5, 2016 (CN) .......................... 2016 1 0207371

(51) Int. Cl.
| C07D 471/14 | (2006.01) |
| C07D 471/22 | (2006.01) |
| A61P 35/00 | (2006.01) |
| A61K 31/519 | (2006.01) |

(52) U.S. Cl.
CPC .......... *C07D 471/14* (2013.01); *A61K 31/519* (2013.01); *A61P 35/00* (2018.01); *C07D 471/22* (2013.01)

(58) Field of Classification Search
CPC ..... C07D 471/14; C07D 471/22; A61P 35/00; A61K 31/519
See application file for complete search history.

(56) References Cited

U.S. PATENT DOCUMENTS 10,059,712 B2    8/2018    Yang et al.

FOREIGN PATENT DOCUMENTS

| CA | 2369448 A1 | 10/2000 |
| CN | 102532144 A | 7/2012 |
| CN | 102579452 A | 7/2012 |
| CN | 103054870 A | 4/2013 |
| CN | 103570727 | * 2/2014 |
| CN | 105330666 A | 2/2016 |
| EP | 3070089 A1 | 9/2016 |
| WO | 03082264 A2 | 10/2003 |
| WO | 2004/064759 A2 | 8/2004 |
| WO | 2004064759 A2 | 8/2004 |

OTHER PUBLICATIONS

Bandekar et al., Jpournal of Medicinal Chemistry, (2010), 53(9), 3558-3565.*
PCT International Search Report and Written Opinion for PCT/CN2017/079371 dated Jul. 10, 2017 (11 pages).
Bandekar et al., "Antimicrobial Activity of Tryptanthrins in *Escherichia coli*," J. Med. Chem., 2010, 53:3558-3565.
Cuiling et al., "Progress in the Synthesis of Natural Product Tryptanthrin and its Derivatives," http://www.cnki.net, 2007, pp. 89-95.
Extended European Search Report of Application No. 17778637.3 dated Aug. 6, 2019.
Bhattacharjee, A.K. et al., Analysis of Stereoelectronic Properties, Mechanism of Action and Pharmacophore of Synthetic Indolo[2,1-b]quinazoline-6,12-dione Derivatives in Relation to Antileishmanial Activity Using Quantum Chemical, Cyclic Voltammetry and 3-D-QSAR Catalyst Procedures, Bioorganic & Medicinal Chemistry, 2002, pp. 1979-1989. vol. 10, No. 6.

(Continued)

*Primary Examiner* — Alexander R Pagano
*Assistant Examiner* — Ebenezer O Sackey
(74) *Attorney, Agent, or Firm* — Eversheds Sutherland (US) LLP

(57) ABSTRACT

This invention discloses the use of aza-tryptanthrin derivatives as an IDO1 and/or TDO inhibitors, and the derivatives are represented by the general Formula (I). The compounds represented by the Formula (I) have inhibitory effects on indoleamine-2,3-dioxygenase 1 (IDO1) and/or tryptophan-2,3-dioxygenase (TDO), and can be used for treating diseases having the pathological features of IDO1 and/or TDO-mediated tryptophan metabolism, including but not limited to tumors, autoimmune disease, infectious diseases, Alzheimer's disease, depression, anxiety.

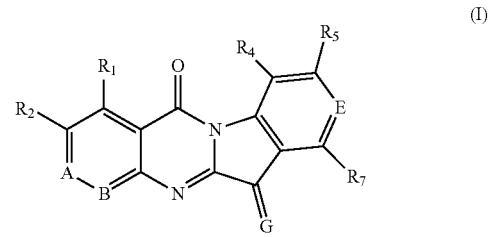

12 Claims, No Drawings

(56) References Cited

OTHER PUBLICATIONS

Scovill, J. et al., Antitrypanosomal Activities of Tryptanthrins, Mar. 2002, pp. 882-883, vol. 46, No. 3.
Bhattacharjee, A.K. et al., Structure-activity relationship study of antimalarial indolo [2,I-b ]quinazoline-6,12-diones (tryptanthrins). Three dimensional pharmacophore modeling and identification of new antimalarial candidates, European Journal of Medicinal Chemistry, 2004, pp. 59-67, vol. 39, No. 1.
Yu, S-T, et al., Cytotoxicity and reversal of multidrug resistance by tryptanthrin-derived indoloquinazolines, Acta Pharmacologica Sinica, 2010, pp. 259-264, vol. 31, No. 2.
Hwang, J-M, et al., Design, Synthesis, and Structure-Activity Relationship Studies of Tryptanthrins as Antitubercular Agents, 2013, pp. 354-367, vol. 76, No. 3.
Yang, S, et al., Discovery of Tryptanthrin Derivatives as Potent Inhibitors of Indoleamine 2,3-Dioxygenase with Therapeutic Activity in Lewis Lung Cancer {LLC) Tumor-Bearing Mice. 2013, Journal of Medicinal Chemistry, pp. 8321-8331, vol. 56, No. 21.

* cited by examiner

USE OF AZA-TRYPTANTHRIN DERIVATIVES AS INHIBITORS OF IDO1 AND/OR TDO

TECHNICAL FIELD

The present application relates to, but is not limited to, the field of medicinal chemistry, and more particularly, to the use of aza-tryptanthrin derivatives as inhibitors of IDO1 and/or TDO which are key enzymes for the metabolism of tryptophan along kynurenine pathway, to the treatment of diseases with pathological features of IDO1 and/or TDO-mediated tryptophan metabolism, including but not limited to tumors, autoimmune diseases, infectious diseases, Alzheimer's disease, depression, and anxiety.

BACKGROUND

Tryptophan, as an essential amino acid in the human body, can only be taken through diet, with a lower content in the body, and the concentration of tryptophan in adult plasma is about 40-80 μM. About 95% of tryptophan is metabolized through kynurenine pathway[Armstrong, M. D. and Stave, U. *Metabolism*. 1973, 22, 561-569.]. Metabolites of this pathway have immunosuppressive effects and play a key role in the tumor immune escape process. The earliest discovered tryptophan metabolism enzyme was tryptophan-2,3-dioxygenase (TDO) [Kotake, Y.; Masayama, I. Z. Physiol. Chem. 1936, 243, 237-244.], and later, indoleamine-2,3-dioxygenase 1 (IDO1) was discovered[Higuchi, K.; Hayaishi, O. 1967, Arch. Biochem. Biophys. 120, 397-403]. Both enzymes can metabolize tryptophan and other indole-containing endogenous substances along the kynurenine pathway, and be the rate-limiting enzymes of this metabolic process. In vivo and in vitro, IDO1 or TDO can oxidatively cleave the 2,3-double bond of the indole ring in tryptophan with the help of molecular oxygen so as to form N-formylkynurenine (NFK), which is further oxidized to form metabolites such as kynurenine, picolinic acid, quinolinic acid and the like (Scheme 1).

Scheme 1: kynurenine pathway of tryptophan metabolism

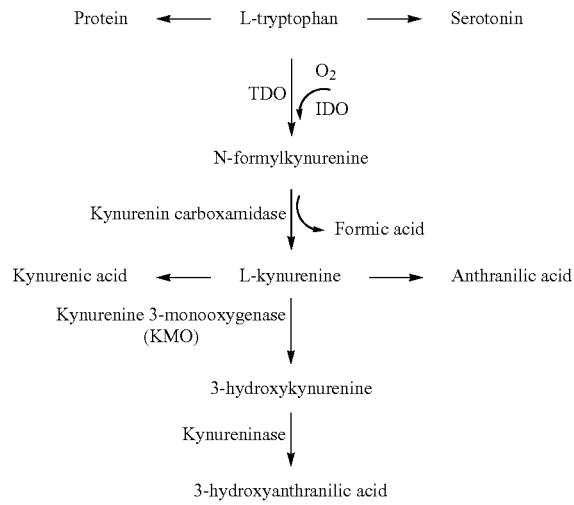

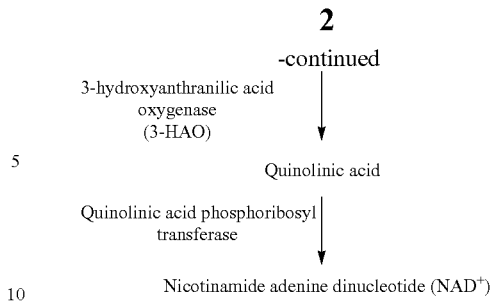

Indoleamine-2,3-dioxygenase 1 (IDO1, EC 1.13.11.52) is the first enzyme that catalyzes the metabolism of tryptophan along kynurenine pathway in mammals, and is also the rate-limiting enzyme, and IDO1 is one of the causes of tumor immune tolerance and is associated with poor prognosis in cancer patients[Platten, M.; Wick, W.; Van den Eynde, B. *J. Cancer Res*. 2012, 72, 5435-5440]. IDO1 is highly expressed in various tumor tissues, which leads to local tryptophan depletion and induces T cells to arrest in G1 phase, thereby inhibiting T cell proliferation; and IDO-dependent tryptophan degradation leads to kynurenine levels increased, also induces oxygen free radicals to mediate T cell apoptosis; and when antigen-presenting cells such as macrophages and dendritic cells overexpress IDO, this may enhance local regulatory T cell (Treg)-mediated immunosuppression, and promote the body's peripheral immune tolerance to tumor-specific antigens. In vitro and in vivo studies have shown that IDO1 inhibitors can enhance the role of tumor therapeutic vaccines, therapeutic monoclonal antibodies, chemotherapy and radiotherapy[Godin-Ethier, J.; Hanafi, L.-A.; Piccirillo, C. A.; Lapointe, R. *Clin. Cancer Res*. 2011, 17, 6985-6991].

IDO1 enhances regulatory T cell-mediated immunosuppression at the site of infection, prompting the body to develop immune tolerance to pathogenic microorganisms, which is closely related to the emergence of antibiotic and antiviral drug resistance. In addition, IDO1 is further closely related to the pathogenesis of various diseases, including autoimmune diseases, Alzheimer's disease, depression, anxiety, cataract and the like. Therefore, IDO1 inhibitors have attracted more and more attention as potential drugs.

Tryptophan-2,3-dioxygenase (TDO) is another important enzyme regulating the metabolism of tryptophan along kynurenine pathway. In recent years, it has become a research hotspot as an inhibitor. Platten et al. confirmed that TDO is highly expressed in human glioma cells. Inhibition by drugs or knockout of TDO can block the release of kynurenine, and on the contrary, knocking out IDO1 does not affect the concentration of kynurenine, and this suggests that TDO is one of the key enzymes for the metabolism of tryptophan in these cells[C. A. Opitz, U. M. Litzenburger, F. Sahm, M. Ott, I. Tritschler, S. Trump, T. Schumacher, L. Jestaedt, D. Schrenk, M. Weller, M. Jugold, G. J. Guillemin, C. L. Miller, C. Lutz, B. Radlwimmer, I. Lehmann, A. von Deimling, W. Wick, M. Platten, Nature. 2011, 478, 197-203.]. In an evaluation study of 104 human tumor cell lines, Van den Eynde et al found that 20 cell lines only express TDO, 17 cell lines only express IDO1, and 16 cell lines express both TDO and IDO1 (malignant glioma, Mesothelioma, head and neck cancer, pancreatic cancer, non-small cell lung cancer, malignant sarcoma, bladder cancer, gallbladder cancer, etc.). That is, IDO1 inhibitors are effective against 32% of tumor cell lines, TDO inhibitors are effective against 35% of tumor cell lines, and IDO1 and TDO dual inhibitors are effective against 51% of tumor cell lines. In theory, dual inhibitors of IDO1 and TDO will further enhance the effectiveness of tumor immunotherapy[L. Pilotte, P. Larrieu, V. Stroobant, D. Colau, E. Dolusic, R. Frederick, E.De Plaen, C. Uyttenhove, J. Wouters, B. Masereel, B. J. Van den Eynde, *Proc. Natl. Acad. Sci. USA* 2012, 109, 2497-2502.].

Tryptanthrin is an indolquinazoline based alkaloid and exists in blue plants such as *Polygonum tinctorium* and *Isatis tinctoria*. Studies have shown that such compounds have antibacterial, antiviral, anti-inflammatory, anti-parasitic, and anti-tumor effects. Qing Yang et al. of Fudan University synthesized a series of tryptanthrin derivatives and tested their inhibitory activity against IDO1. Among them, the fluorine-substituted tryptanthrin derivative (structure is as follows) has good activity, and the $IC_{50}$ value of recombinant human IDO-1 is 0.534 μM, and this compound can promote the proliferation of T cells, and the surface plasmon resonance (SPR) experiment proves that the compound can be directly bound to IDO1, and the $K_D$ value is 46.8 μM [Yang, S.; Li, X.; Hu, F.; Li, Y.; Yang, Y.; Yan, J.; Kuang, C.; Yang, Q. *J. Med. Chem.* 2013, 56, 8321-8231]. Qing Yang et al. also introduced an aminomethyl substituent at the 3-position of tryptanthrin and found no significant change in the activity of inhibiting IDO1 (WO 2015070766).

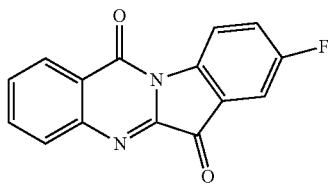

Valliante et al. synthesized a series of tryptanthrin and aza-tryptanthrin derivatives and found that these compounds contribute to the production of TNF-α, and some compounds can have effects at a concentration of 5 μM or lower (U.S. Pat. No. 8,193,185B2). However, this patent does not relate to the IDO1 and TDO targets, and the results of the study also indicate that the introduction of nitrogen atom in the benzene ring is not directly related to the activity, and wherein the 8-nitro-1-aza-tryptanthrin did not exhibit activity at concentration up to 20 μM.

SUMMARY

The following is a summary of the subject matters described in detail in this specification. This summary is not intended to limit the scope of the claims.

The present inventors have surprisingly discovered aza-tryptanthrin derivatives having significant indoleamine-2,3-dioxygenase 1 and/or tryptophan-2,3-dioxygenase inhibiting activities.

In some embodiments of the present invention, provided herein the use of the aza-tryptanthrin derivatives as indoleamine-2,3-dioxygenase 1 and/or tryptophan-2,3-dioxygenase inhibitors.

In some embodiments of the present invention, provided herein novel aza-tryptanthrin derivatives.

In some embodiments of the present invention, provided herein a process for preparing the novel aza-tryptanthrin derivatives described above.

In some embodiment of the present invention, provided herein pharmaceutical compositions comprising the novel aza-tryptanthrin derivatives described above.

DETAILED DESCRIPTION

Specifically, in one aspect, some embodiments of the present invention provides the use of aza-tryptanthrin derivatives as indoleamine-2,3-dioxygenase 1 and/or tryptophan-2,3-dioxygenase inhibitors, which are represented by Formula (I), or geometric isomers, tautomers, isotopic labelings, hydrates, solvates, metabolites, pharmaceutically acceptable salt or prodrug thereof:

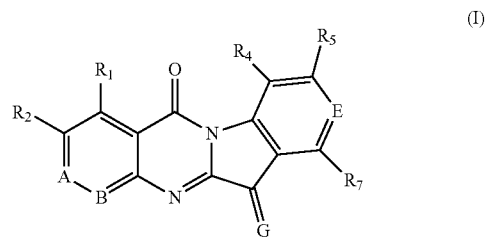

wherein, in the Formula (I),
one of A and B is N and the other is C—$R_3$;
E is N or —C—$R_6$;
G is O or N—Y—Z, wherein Y is —O—, and Z is hydrogen, an unsubstituted or substituted C1-C4 alkyl group, an unsubstituted or substituted C2-C4 alkenyl group, an unsubstituted or substituted C2-C4 alkynyl group, a carboxymethyl group (—$CH_2C(=O)OH$), a sulfonyl group (—$S(=O)_2OH$), or a phosphoryl group (—$P(=O)(OH)_2$); and alternatively, Y is —N(H)—, and Z is hydrogen, —C(=S)—N($R_8$)($R_9$), —C(=O)—N($R_8$)($R_9$), or —C(=N)—N($R_8$)($R_9$);
$R_1$ to $R_7$ are each independently selected from hydrogen, an unsubstituted or substituted C1-C4 alkyl group, an unsubstituted or substituted C1-C4 alkoxy group, halogen, a nitro group, a cyano group, a methylsulfonyl group or a hydroxyl group;
$R_8$ and $R_9$ are each independently selected from hydrogen or an unsubstituted C1-C4 alkyl group.

In some embodiments of the present invention, the embodiment of the present invention provides the use of aza-tryptanthrin derivatives as IDO1 and/or TDO inhibitors, wherein the unsubstituted C1-C4 alkyl group is selected from a methyl group, an ethyl group, a n-propyl group, an iso-propyl group, a n-butyl group, an iso-butyl group, or a tert-butyl group. The substituted C1-C4 alkyl group means that the hydrogen at any position of the carbon chain thereof is substituted by an optional one of the following groups: halogen, a hydroxyl group, an amino group, or —N($R_{10}$)($R_{11}$), wherein, $R_{10}$ and $R_{11}$ are each independently selected from hydrogen or an unsubstituted C1-C4 alkyl group; for example, a trifluoromethyl group, a 2-hydroxyethyl group, a 2-(dimethylamino)ethyl group, or a 3-(dimethylamino)propyl group, or a nitrogen-containing 4-7-membered heterocyclic group (for example, a tetrahydropyrrole group, a piperidine group, a morpholine group, a piperazine group, a homopiperazine group, etc.) formed by $R_{10}$ and $R_{11}$ together with N.

In some embodiments of the present invention, the embodiment of the present invention provides the use of aza-tryptanthrin derivatives as IDO1 and/or TDO inhibitors, wherein the unsubstituted C1-C4 alkoxy group is selected from a methoxy group, an ethoxy group, a n-propoxy group, an iso-propoxy group, a n-butoxy group, an iso-butoxy group, or a tert-butoxy group. The substituted C1-C4 alkoxy group means that the hydrogen at any position of the carbon chain thereof is substituted by an optional one of the following groups: halogen, a hydroxyl group, an amino group, or —N($R_{10}$)($R_{11}$), wherein, $R_{10}$ and $R_{11}$ are each independently selected from hydrogen or an unsubstituted C1-C4 alkyl group; for example, a trifluoromethoxy group, a 2-hydroxyethoxy group, a 2-(dimethylamino)ethoxy group, or a 3-(dimethylamino)propoxy group.

In some embodiments of the present invention, the embodiment of the present invention provides the use of aza-tryptanthrin derivatives as IDO1 and/or TDO inhibitors, wherein the unsubstituted C2-C4 alkenyl group is selected from a vinyl group, an allyl group, a 1-butenyl group, a 2-butenyl group and the like. The substituted C2-C4 alkenyl group indicates that the hydrogen at any position of the carbon chain thereof is substituted by an optional one of the following groups: halogen, or a hydroxyl group and the like.

In some embodiments of the present invention, the embodiment of the present invention provides the use of aza-tryptanthrin derivatives as IDO1 and/or TDO inhibitors, wherein the unsubstituted C2-C4 alkynyl group is selected from a ethynyl group, a propynyl group, a butynyl group and the like. The substituted C2-C4 alkynyl group means that the hydrogen at any position of the carbon chain thereof is substituted by an optional one of the following groups: halogen, or a hydroxyl group.

In some embodiments of the present invention, the embodiment of the present invention provides the use of aza-tryptanthrin derivatives as IDOL and/or TDO inhibitors, wherein the halogen is fluorine, chlorine, bromine, or iodine.

In one embodiment of the present invention, the embodiment of the present invention provides the use of aza-tryptanthrin derivatives as IDO1 and/or TDO inhibitors, the derivatives being represented by the Formula (I), wherein G is O; A is N, and B is —CH, or B is N and A is —CH.

In one embodiment of the present invention, the embodiment of the present invention provides the use of aza-tryptanthrin derivatives as IDO1 and/or TDO inhibitors, the derivatives being represented by the Formula (I), wherein G is O; A is N, and B is —CH, or B is N and A is —CH; and E is N.

In one embodiment of the present invention, the embodiment of the present invention provides the use of aza-tryptanthrin derivatives as IDO1 and/or TDO inhibitors, the derivatives being represented by the Formula (I), wherein G is O; A is N, and B is —CH, or B is N and A is —CH;
and E is —C—$R_6$;
$R_1$, $R_2$, $R_4$ to $R_7$ are each independently selected from hydrogen, an unsubstituted or substituted C1-C4 alkyl group, an unsubstituted or substituted C1-C4 alkoxy group, halogen, a nitro group, a cyano group, a methylsulfonyl group or a hydroxyl group.

In one embodiment of the present invention, the embodiment of the present invention provides the use of aza-tryptanthrin derivatives as IDO1 and/or TDO inhibitors, the derivatives being represented by the Formula (I), wherein G is O; A is N, and B is —CH, or B is N and A is —CH;
and E is —C—$R_6$;
$R_1$ and $R_2$ are hydrogen, and $R_4$ to $R_7$ are each independently selected from hydrogen, an unsubstituted or substituted C1-C4 alkyl group, an unsubstituted or substituted C1-C4 alkoxy group, halogen, a nitro group, a cyano group, a methylsulfonyl group or a hydroxyl group.

In one embodiment of the present invention, the embodiment of the present invention provides the use of aza-tryptanthrin derivatives as IDO1 and/or TDO inhibitors, the derivatives being represented by the Formula (I), wherein G is O; A is N, and B is —CH, or B is N and A is —CH;
and E is —C—$R_6$;
$R_1$ and $R_2$ are hydrogen, and $R_4$ to $R_7$ are each independently selected from hydrogen, a methyl group, a trifluoromethoxy group, a methoxy group, fluorine, chlorine, bromine, a nitro group, a cyano group, a methylsulfonyl group or a hydroxyl group.

In one embodiment of the present invention, the embodiment of the present invention provides the use of aza-tryptanthrin derivatives as IDO1 and/or TDO inhibitors, the derivatives being represented by the Formula (I), wherein G is N—Y—Z, and wherein Y is —O—, and Z is hydrogen, an unsubstituted or substituted C1-C4 alkyl group, an unsubstituted or substituted C2-C4 alkenyl group, an unsubstituted or substituted C2-C4 alkynyl group, a carboxymethyl group (—$CH_2C$(=O)OH), a sulfonyl group (—S(=O)$_2$OH), or a phosphoryl group (—P(=O)(OH)$_2$); and alternatively, Y is —N(H)—, and Z is hydrogen, —C(=S)—N($R_8$)($R_9$), —C(=O)—N($R_8$)($R_9$), or —C(=N)—N($R_8$)($R_9$); A is N and B is —CH, or B is N and A is —CH.

In one embodiment of the present invention, the embodiment of the present invention provides the use of aza-tryptanthrin derivatives as IDO1 and/or TDO inhibitors, the derivatives being represented by the Formula (I), wherein G is N—Y—Z, and wherein Y is —O—, and Z is hydrogen, an unsubstituted or substituted C1-C4 alkyl group, an unsubstituted or substituted C2-C4 alkenyl group, an unsubstituted or substituted C2-C4 alkynyl group, a carboxymethyl group (—$CH_2C$(=O)OH), a sulfonyl group (—S(=O)$_2$OH), or a phosphoryl group (—P(=O)(OH)$_2$); and alternatively, Y is —N(H)—, and Z is hydrogen, —C(=S)—N($R_8$)($R_9$), —C(=O)—N($R_8$)($R_9$), or —C(=N)—N($R_8$)($R_9$); A is N and B is —CH, or B is N and A is —CH; and E is N.

In one embodiment of the present invention, the embodiment of the present invention provides the use of aza-tryptanthrin derivatives as IDO1 and/or TDO inhibitors, the derivatives being represented by the Formula (I), wherein G is N—Y—Z, and wherein Y is —O—, and Z is hydrogen, an unsubstituted or substituted C1-C4 alkyl group, an unsubstituted or substituted C2-C4 alkenyl group, an unsubstituted or substituted C2-C4 alkynyl group, a carboxymethyl group (—$CH_2C$(=O)OH), a sulfonyl group (—S(=O)$_2$OH), or a phosphoryl group (—P(=O)(OH)$_2$); and alternatively, Y is —N(H)—, and Z is hydrogen, —C(=S)—N($R_8$)($R_9$), —C(=O)—N($R_8$)($R_9$), or —C(=N)—N($R_8$)($R_9$); A is N and B is —CH, or B is N and A is —CH;
and E is —C—$R_6$;
$R_1$, $R_2$, and $R_4$ to $R_7$ are each independently selected from hydrogen, an unsubstituted or substituted C1-C4 alkyl group, an unsubstituted or substituted C1-C4 alkoxy group, halogen, a nitro group, a cyano group, a methylsulfonyl group or a hydroxyl group.

In one embodiment of the present invention, the embodiment of the present invention provides the use of aza-tryptanthrin derivatives as IDO1 and/or TDO inhibitors, the derivatives being represented by the Formula (I), wherein G is N—Y—Z, and wherein Y is —O—, and Z is hydrogen, an unsubstituted or substituted C1-C4 alkyl group, an unsubstituted or substituted C2-C4 alkenyl group, an unsubstituted or substituted C2-C4 alkynyl group, a carboxymethyl group (—$CH_2C$(=O)OH), a sulfonyl group (—S(=O)$_2$OH), or a phosphoryl group (—P(=O)(OH)$_2$); and alternatively, Y is —N(H)—, and Z is hydrogen, —C(=S)—N($R_8$)($R_9$), —C(=O)—N($R_8$)($R_9$), or —C(=N)—N($R_8$)($R_9$); A is N and B is —CH, or B is N and A is —CH;

and E is —C—R$_6$;

R$_1$ and R$_2$ are hydrogen, and R$_4$ to R$_7$ are each independently selected from hydrogen, an unsubstituted or substituted C1-C4 alkyl group, an unsubstituted or substituted C1-C4 alkoxy group, halogen, a nitro group, a cyano group, a methylsulfonyl group or a hydroxyl group.

In one embodiment of the present invention, the embodiment of the present invention provides the use of aza-tryptanthrin derivatives as IDO1 and/or TDO inhibitors, the derivatives being represented by the Formula (I), wherein G is N—Y—Z, and wherein Y is —O—, and Z is hydrogen, an unsubstituted or substituted C1-C4 alkyl group, an unsubstituted or substituted C2-C4 alkenyl group, an unsubstituted or substituted C2-C4 alkynyl group, a carboxymethyl group (—CH$_2$C(=O)OH), a sulfonyl group (—S(=O)$_2$OH), or a phosphoryl group (—P(=O)(OH)$_2$); and alternatively, Y is —N(H)—, and Z is hydrogen, —C(=S)—N(R$_8$)(R$_9$), —C(=O)—N(R$_8$)(R$_9$), or —C(=N)—N(R$_8$)(R$_9$); A is N and B is —CH, or B is N and A is —CH;

and E is —C—R$_6$;

R$_1$ and R$_2$ are hydrogen, and R$_4$ to R$_7$ are each independently selected from hydrogen, a methyl group, a trifluoromethoxy group, a methoxy group, fluorine, chlorine, bromine, a nitro group, a cyano group, a methylsulfonyl group or a hydroxyl group.

In some embodiments of the present invention, the embodiment of the present invention provides the use of compounds represented by the above Formula (I), and the compounds are selected from the group consisting of:

pyrido[2',3': 4,5]pyrimido[1,2-α]indole-5,11-dione (Compound CY-1-1);
9-fluoropyrido[2',3':4,5]pyrimido[1,2-α]indole-5,11-dione (Compound CY-1-2);
9-(trifluoromethoxy)pyrido[2',3':4,5]pyrimido[1,2-α]indole-5,11-dione (Compound CY-1-3);
9-nitropyridine[2',3':4,5]pyrimido[1,2-α]indole-5,11-dione (Compound CY-1-4);
9-chloropyrido[2',3':4,5]pyrimido[1,2-α]indole-5,11-dione (Compound CY-1-5);
9-methoxypyrido[2',3':4,5]pyrimido[1,2-α]indole-5,11-dione (Compound CY-1-6);
9-methylpyrido[2',3':4,5]pyrimido[1,2-α]indole-5,11-dione (Compound CY-1-7);
pyrido[3',4':4,5]pyrimido[1,2-α]indole-5,11-dione (Compound CY-1-8);
9-methoxypyrido[3',4':4,5]pyrimido[1,2-α]indole-5,11-dione (Compound CY-1-9);
9-chloropyrido[3',4':4,5]pyrimido[1,2-α]indole-5,11-dione (Compound CY-1-10);
9-fluoropyrido[3',4':4,5]pyrimido[1,2-α]indole-5,11-dione (Compound CY-1-11);
11-(hydroxyimino)pyrido[2',3':4,5]pyrimido[1,2-α]indol-5(11H)-one (Compound CY-1-12);
9-chloro-11-(hydroxyimino)pyrido[2',3':4,5]pyrimido[1,2-α]indole-5(11H)-one (Compound CY-1-13);
11-(hydroxyimino)-9-methylpyrido[2',3':4,5]pyrimido[1,2-α]indole-5(11H)-one (Compound CY-1-14);
11-(hydroxyimino)-9-methoxypyrido[2',3':4,5]pyrimido[1,2-α]indole-5(11H)-one (Compound CY-1-15);
11-((2-(dimethylamino)ethoxy)imino)pyrido[2',3':4,5]pyrimido[1,2-α]indole-5(11H)-one (Compound CY-1-16);
11-((2-(dimethylamino)ethoxy)imino)-9-nitropyrido[2',3':4,5]pyrimido[1,2-a]indol-5(11H)-one (Compound CY-1-17);
9-chloro-11-((2-(dimethylamino)ethoxy)imino)pyrido[2',3':4,5]pyrimido[1,2-α]indol-5(11H)-one (Compound CY-1-18);
11-((2-(dimethylamino)ethoxy)imino)-9-fluoropyrido[2',3':4,5]pyrimido[1,2-a]indol-5(11H)-one (Compound CY-1-19);
9-chloro-11-((3-(dimethylamino)propoxy)imino)pyrido[2',3':4,5]pyrimido[1,2-α]indol-5(11H)-one (Compound CY-1-20);
11-((2-hydroxyethoxy)imino)-9-nitropyrido[2',3':4,5]pyrimido[1,2-α]indol-5(11H)-one (Compound CY-1-21);
N,N-dimethyl-2-(9-nitro-5-oxopyrido[2',3':4,5]pyrimido[1,2-α]indol-11(5H)-ylidene)hydrazine-1-carbothioamide (Compound CY-1-22);
2-(9-nitro-5-oxopyrido[2',3':4,5]pyrimido[1,2-α]indol-11(5H)-ylidene)hydrazine-1-carboximidamide (Compound CY-1-23);
(((9-nitro-5-oxopyrido[2',3':4,5]pyrimido[1,2-α]indol-11(5H)-ylidene)amino)oxy)sulfonic acid (Compound CY-1-24);
11-(methoxyimino)-9-nitropyrido[2',3':4,5]pyrimido[1,2-α]indol-5(11H)-one (Compound CY-1-25);
11-(ethoxyimino)-9-nitropyrido[2',3':4,5]pyrimido[1,2-α]indol-5(11H)-one (Compound CY-1-26);
11-((allyloxy)imino)-9-nitropyrido[2',3':4,5]pyrimido[1,2-α]indol-5(11H)-one (Compound CY-1-27);
11-((carboxymethoxyimino)-9-nitropyridine[2',3':4,5]pyrimido[1,2-α]indole-5(11H)-one (Compound CY-1-28);
2-(9-nitro-5-oxopyrido[2',3':4,5]pyrimido[1,2-α]indol-11(5H)-ylidene)hydrazine-1-carbothioamide (Compound CY-1-29);
2-(9-methoxy-5-oxopyrido[2',3':4,5]pyrimido[1,2-α]indol-11(5H)-ylidene)-N,N-dimethyl-hydrazine-1-carbothioamide (Compound CY-1-30);
pyrido[2,3-D]pyrido[3',4':4,5]pyrrolo[1,2-α]pyrimidine-5,11-dione (Compound CY-1-31);
2-(9-chloro-5-oxopyrido[2',3':4,5]pyrimido[1,2-α]indol-11(5H)-ylidene)hydr azine-1-carboximidamide (Compound LDB-1-1);
2-(9-chloro-5-oxopyrido[2',3':4,5]pyrimido[1,2-α]indol-11(5H)-ylidene)hydr azine-1-carbothioamide (Compound LDB-1-2);
2-(9-(trifluoromethoxy)-5-oxopyrido[2',3':4,5]pyrimido[1,2-α]indol-11 (5H)-ylidene)hydrazine-1-carboximidamide (Compound LDB-1-3);
2-(9-(trifluoromethoxy)-5-oxopyrido[2',3':4,5]pyrimido[1,2-α]indol-11 (5H)-ylidene)hydrazine-1-carbothioamide (Compound LDB-1-4);
2-(9-chloro-5-oxopyrido[3',4':4,5]pyrimido[1,2-α]indol-11(5H)-ylidene)hydr azine-1-carboximidamide (Compound LDB-1-5); and
2-(9-chloro-5-oxopyrido[3',4':4,5]pyrimido[1,2-α]indol-11(5H)-ylidene)hydr azine-1-carbothioamide (Compound LDB-1-6).

An embodiment of the invention provides the use of compounds of Formula (I) for the treatment of diseases having pathological features of IDO1 and/or TDO-mediated tryptophan metabolism, and these diseases includes but not limited to tumors, infectious diseases, and autoimmune disease, Alzheimer's disease, depression, anxiety. The reference dosage for each dose of human is 0.1-20 mg/kg body weight, which is administered orally or by injection.

In a second aspect, an embodiment of the present invention provides novel aza-tryptanthrin derivatives as IDO1 and/or TDO inhibitors, represented by the Formula (II), or geometric isomers, tautomers, isotopic labels, hydrates, solvates, metabolites, pharmaceutically acceptable salt or prodrug thereof:

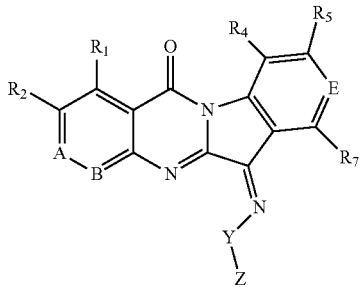

(II)

wherein, in Formula (II), one of A and B is N, and the other is C—R₃;

E is N or —C—R₆;

Y is —O—, and Z is hydrogen, an unsubstituted or substituted C1-C4 alkyl group, an unsubstituted or substituted C2-C4 alkenyl group, an unsubstituted or substituted C2-C4 alkynyl group, a carboxymethyl group (—CH₂C(=O)OH), a sulfonyl group (—S(=O)₂OH), or a phosphoryl group (—P(=O)(OH)₂); and alternatively, Y is —N(H)—, and Z is hydrogen, —C(=S)—N(R₈)(R₉), —C(=O)—N(R₈)(R₉), or —C(=N)—N(R₈)(R₉);

R₁ to R₇ are each independently selected from hydrogen, an unsubstituted or substituted C1-C4 alkyl group, an unsubstituted or substituted C1-C4 alkoxy group, halogen, a nitro group, a cyano group, a methylsulfonyl group or a hydroxy group;

R₈ and R₉ are each independently selected from hydrogen or an unsubstituted C1-C4 alkyl group.

In one embodiment of the present invention, the embodiment of the present invention provides novel aza-tryptanthrin derivatives represented by the Formula (II), wherein A is N, and B is —CH, or B is N and A is —CH.

In one embodiment of the present invention, the embodiment of the present invention provides novel aza-tryptanthrin derivatives represented by the Formula (II), wherein A is N, and B is —CH, or B is N and A is —CH; and E is N.

In one embodiment of the present invention, the embodiment of the present invention provides novel aza-tryptanthrin derivatives represented by the Formula (II), wherein A is N, and B is —CH, or B is N and A is —CH;

and E is —C—R₆;

R₁, R₂, and R₄ to R₇ are each independently selected from hydrogen, an unsubstituted or substituted C1-C4 alkyl group, an unsubstituted or substituted C1-C4 alkoxy group, halogen, a nitro group, a cyano group, a methylsulfonyl group or a hydroxy group.

In one embodiment of the present invention, the embodiment of the present invention provides novel aza-tryptanthrin derivatives represented by the Formula (II), wherein A is N, and B is —CH, or B is N and A is —CH;

and E is —C—R₆;

R₁ and R₂ are hydrogen, and R₄ to R₇ are each independently selected from hydrogen, an unsubstituted or substituted C1-C4 alkyl group, an unsubstituted or substituted C1-C4 alkoxy group, halogen, a nitro group, a cyano group, a methylsulfonyl group or a hydroxy group.

In one embodiment of the present invention, the embodiment of the present invention provides novel aza-tryptanthrin derivatives represented by the Formula (I), wherein A is N, and B is —CH, or B is N and A is —CH;

and E is —C—R₆;

R₁ and R₂ are hydrogen, and R₄ to R₇ are each independently selected from hydrogen, a methyl group, a trifluoromethoxy group, a methoxy group, fluorine, chlorine, bromine, a nitro group, a cyano group, a methylsulfonyl group or a hydroxy group;

Y is —O—, and Z is hydrogen, an unsubstituted or substituted C1-C4 alkyl group, an unsubstituted or substituted C2-C4 alkenyl group, an unsubstituted or substituted C2-C4 alkynyl group, a carboxymethyl group (—CH₂C(=O)OH), a sulfonyl group (—S(=O)₂OH), or a phosphoryl group (—P(=O)(OH)₂); and alternatively, Y is —N(H)—, and Z is hydrogen, —C(=S)—N(R₈)(R₉), —C(=O)—N(R₈)(R₉), or —C(=N)—N(R₈)(R₉);

R₈ and R₉ are each independently selected from hydrogen or an unsubstituted C1-C4 alkyl group.

In some embodiments of the present invention, the embodiment of the present invention provides novel aza-tryptanthrin derivatives, and the compounds are selected from the group consisting of:

11-(hydroxyimino)pyrido[2',3':4,5]pyrimido[1,2-α]indol-5(11H)-one (Compound CY-1-12);

9-chloro-11-(hydroxyimino)pyrido[2',3':4,5]pyrimido[1,2-α]indole-5 (11H)-one (Compound CY-1-13);

11-(hydroxyimino)-9-methylpyrido[2',3':4,5]pyrimido[1,2-α]indole-5 (11H)-one (Compound CY-1-14);

11-(hydroxyimino)-9-methoxypyrido[2',3':4,5]pyrimido[1,2-α]indole-5(11H)-one (Compound CY-1-15);

11-((2-(dimethylamino)ethoxy)imino)pyrido[2',3':4,5]pyrimido[1,2-α]indole-5(11H)-one (Compound CY-1-16);

11-((2-(dimethylamino)ethoxy)imino)-9-nitropyrido[2',3':4,5]pyrimido[1,2-a]indol-5(11H)-one (Compound CY-1-17);

9-chloro-11-((2-(dimethylamino)ethoxy)imino)pyrido[2',3':4,5]pyrimido[1,2-α]indol-5(11H)-one (Compound CY-1-18);

11-((2-(dimethylamino)ethoxy)imino)-9-fluoropyrido[2',3':4,5]pyrimido[1,2-a]indol-5(11H)-one (Compound CY-1-19);

9-chloro-11-((3-(dimethylamino)propoxy)imino)pyrido[2',3':4,5]pyrimido[1,2-α]indol-5(11H)-one (Compound CY-1-20);

11-((2-hydroxyethoxy)imino)-9-nitropyrido[2',3':4,5]pyrimido[1,2-α]indol-5(11H)-one (Compound CY-1-21);

N,N-dimethyl-2-(9-nitro-5-oxopyrido[2',3':4,5]pyrimido[1,2-α]indol-11 (5H)-ylidene)hydrazine-1-carbothioamide (Compound CY-1-22);

2-(9-nitro-5-oxopyrido[2',3':4,5]pyrimido[1,2-α]indol-11 (5H)-ylidene)hydrazine-1-carboximidamide (Compound CY-1-23);

(((9-nitro-5-oxopyrido[2',3':4,5]pyrimido[1,2-α]indol-11 (5H)-ylidene)amino)oxy)sulfonic acid (Compound CY-1-24);

11-(methoxyimino)-9-nitropyrido[2',3':4,5]pyrimido[1,2-α]indol-5 (11H)-one (Compound CY-1-25);

11-(ethoxyimino)-9-nitropyrido[2',3': 4,5]pyrimido[1,2-α]indol-5 (11H)-one (Compound CY-1-26);

11-((allyloxy)imino)-9-nitropyrido[2',3':4,5]pyrimido[1,2-α]indol-5 (11H)-one (Compound CY-1-27);

11-((carboxymethoxyimino)-9-nitropyridine[2',3':4,5]pyrimido[1,2-α]indole-5(11H)-one (Compound CY-1-28);

2-(9-nitro-5-oxopyrido[2',3': 4,5]pyrimido[1,2-α]indol-11 (5H)-ylidene)hydrazine-1-carbothioamide (Compound CY-1-29);

2-(9-methoxy-5-oxopyrido[2',3':4,5]pyrimido[1,2-α]indol-11 (5H)-ylidene)-N,N-dimethyl-hydrazine-1-carbothioamide (Compound CY-1-30);

pyrido[2,3-D]pyrido[3',4':4,5]pyrrolo[1,2-α]pyrimidine-5, 11-dione (Compound CY-1-31);
2-(9-chloro-5-oxopyrido[2',3':4,5]pyrimido[1,2-α]indol-11 (5H)-ylidene)hydr azine-1-carboximidamide (Compound LDB-1-1);
2-(9-chloro-5-oxopyrido[2',3':4,5]pyrimido[1,2-α]indol-11 (5H)-ylidene)hydr azine-1-carbothioamide (Compound LDB-1-2);
2-(9-(trifluoromethoxy)-5-oxopyrido[2',3':4,5]pyrimido[1, 2-α]indol-11 (5H)-ylidene)hydrazine-1-carboximidamide (Compound LDB-1-3);
2-(9-(trifluoromethoxy)-5-oxopyrido[2',3:4,5]pyrimido[1,2-α]indol-11 (5H)-ylidene)hydrazine-1-carbothioamide (Compound LDB-1-4);
2-(9-chloro-5-oxopyrido[3',4':4,5]pyrimido[1,2-α]indol-11 (5H)-ylidene)hydr azine-1-carboximidamide (Compound LDB-1-5); and
2-(9-chloro-5-oxopyrido[3',4':4,5]pyrimido[1,2-α]indol-11 (5H)-ylidene)hydr azine-1-carbothioamide (Compound LDB-1-6).

In a third aspect, an embodiment of the present invention provides a process for preparing aza-tryptanthrin derivatives represented by the Formula (II), comprising the steps of:
reacting compounds of the Formula (III) with compounds of the Formula (IV) to get compounds of the Formula (II'), which are further reacted with compounds of the Formula (V) to get compounds of the Formula (II),

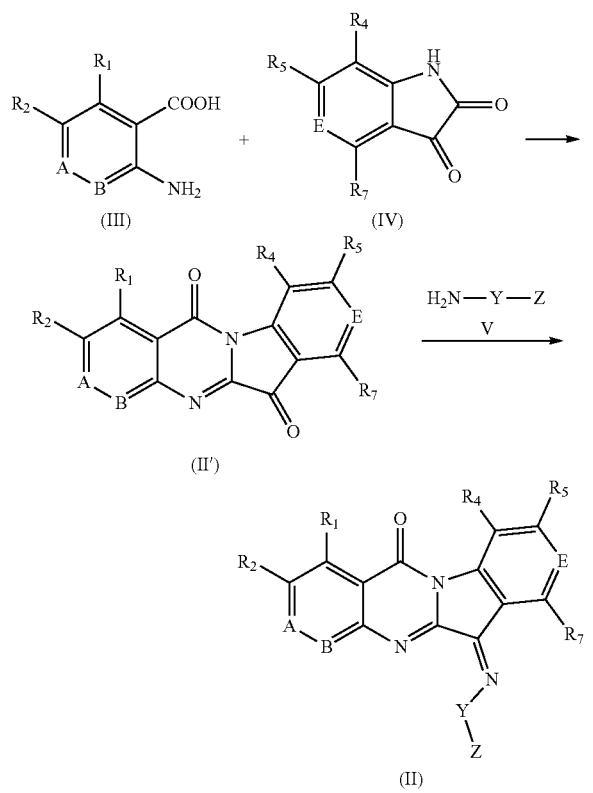

wherein, the definitions of the substituents A, B, E, Y, Z and $R_1$, $R_2$, $R_4$, $R_5$ and $R_7$ involved in the compounds of the Formulae (III), (IV), (V), (II') are defined as those in the aforementioned compounds of the Formula (II).

The process for preparing the aza-tryptanthrin derivatives represented by the Formula (II) provided by the embodiment of the present invention, more particularly, may be referred to the following procedure:

The isatin derivative IV (0.9 mmol) and 1,8-diazabicycloundec-7-ene (abbreviated as DBU, 2.0 mmol) were dissolved in DMF (3 mL) and stirred at room temperature for ten minutes to get solution (1). 2-Aminonicotinic acid analog III (1 mmol), N-methylmorpholine (1.8 mmol), and HBTU (1.0 mmol) were dissolved in DMF (3 mL) to get solution (2). The solution (1) was added dropwise to the solution (2), and stirred at room temperature for 20 h, and the reaction was completed by monitoring with TLC, and then the solvent was evaporated to dryness, and then purified by column chromatography (dichloromethane-methanol mixture eluting solvent) to furnish the compound of Formula (II') as a solid.

The solid obtained by the above reaction and the amino group-containing compound V or its hydrochloride (1 mmol) are dissolved in methanol (10 mL), and heated under reflux overnight, until the reaction is complete, and the solid is precipitated to obtain the compound of the Formula II; or the solvent is evaporated to dryness and purified by column chromatography (dichloromethane-methanol mixture eluting solvent).

In a fourth aspect, an embodiment of the invention provides a pharmaceutical composition comprising the novel tryptanthrin derivatives described above. The pharmaceutical composition comprises a pharmacologically effective amount of a compound of Formula (II) and a pharmaceutically acceptable excipient. These excipients are known to those skilled in the art, for example, physiological saline, gelatin, gum arabic, lactose, microcrystalline cellulose, starch, modified starch, cellulose, modified cellulose, sodium glycolate, calcium hydrogen phosphate, magnesium stearate, talc, colloidal silica, and the like. Further, these compositions may further comprise: stabilizers, wetting agents, emulsifiers, sweeteners, flavoring agents, buffers and the like.

The pharmaceutical composition comprising the above-mentioned tryptanthrin derivatives provided by the embodiment of the present invention can be formulated into a solid or liquid form for oral administration, such as a tablet, a pill, an oral solution, etc., and a sterile solution, suspension or emulsion and the like form for parenteral administration, as needed.

Compared with the compounds (5a, 5b, 5c, 5i) of the Yangqing research group of Fudan University (see Table 1 below), the embodiment of the present invention introduces a nitrogen atom into a specific position of the tryptophan structure, and the resulting new derivatives have an unexpected improvement in the inhibitory activity of the enzyme IDO1, up to more than 100 times. Moreover, the compounds of the embodiments of the present invention also have significant inhibitory activity against TDO.

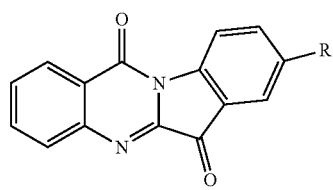 [SMILES: O=C1c2cc(F)ccc2-n2c1nc1ccccc1c2=O]

5a: R = —H
5b: R = —CH$_3$
5c: R = —F
5i: R = —NO$_2$

TABLE 1

Comparison of inhibitory activity of the IDO1 (IC$_{50}$, μM)

| Compound No. | IC$_{50}$ |
|---|---|
| 5a | ++ |
| CY-1-1 | +++ |
| CY-1-8 | +++ |
| 5b | + |
| CY-1-7 | +++ |
| 5c | +++ |
| CY-1-2 | ++++ |
| CY-1-11 | +++ |
| 5i | +++ |
| CY-1-4 | ++++ |

Notes:
++++ = 0.001-0.10 μM;
+++ = 0.10-1.0 μM;
++ = 1.1-10 μM;
+ >10 μM.

The embodiments of the present invention are exemplified below by way of examples, and those skilled in the art, based on the teachings of the embodiments of the present invention, according to the prior art, the improvements of the embodiments of the present invention are still within the scope of protection of the embodiments of the present invention.

The methylene chloride, methanol, N,N-dimethylformamide and the like used in the reaction processes are all commercially available analytical reagents, and are dried and re-steamed according to literature methods; other reagents and raw materials are domestically analytical pure or chemical pure reagents.

The melting point was measured by XT5B or X-4 type precision micro melting point meter (temperature control type) (Beijing Fukai Instrument Co., Ltd.), and the temperature was not corrected. Nuclear magnetic resonance spectroscopy ($^1$H NMR, $^{13}$C NMR) was determined using Bruker NMR system 400 MHz superconducting nuclear magnetic resonance spectrometer with TMS as an internal standard.

Example 1

Compound CY-1-1: pyrido[2',3':4,5]pyrimido[1,2-α]indole-5,11-dione

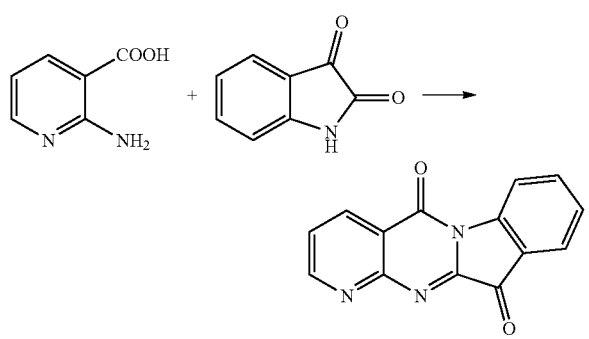

Isatin (0.9 mmol) and DBU (2 mmol) were dissolved in DMF (3 ml) and stirred at room temperature for ten minutes. 2-Aminonicotinic acid (1 mmol), N-methylmorpholine (1.8 mmol) and HBTU (1 mmol) were dissolved in DMF (3 ml), and a solution of the reacted isatin and DBU was added dropwise to the solution at room temperature, and after stirring for 20 h, the reaction was completed by monitoring with TLC, and then the solvent was evaporated to dryness, and then purified by column chromatography (dichloromethane:methanol=80:1) to furnish an orange-yellow solid, yield: 59%. 41 NMR (400 MHz, DMSO-d$_6$) δ 9.08 (dd, J=4.6, 2.0 Hz, 1H), 8.71 (dd, J=7.9, 2.0 Hz, 1H), 8.45 (d, J=8.0 Hz, 1H), 7.90 (t, J=7.9, 4.4 Hz, 2H), 7.75 (dd, J=7.9, 4.6 Hz, 1H), 7.51 (t, J=7.6, 0.7 Hz, 1H). $^{13}$C NMR (101 MHz, DMSO-d$_6$) δ 182.28, 158.08, 157.20, 156.11, 147.63, 145.70, 137.90, 136.30, 127.23, 124.92, 124.70, 122.14, 119.17, 116.89.

Example 2

Compound CY-1-2: 9-fluoropyrido[2',3':4,5]pyrimido[1,2-c]indole-5,11-dione

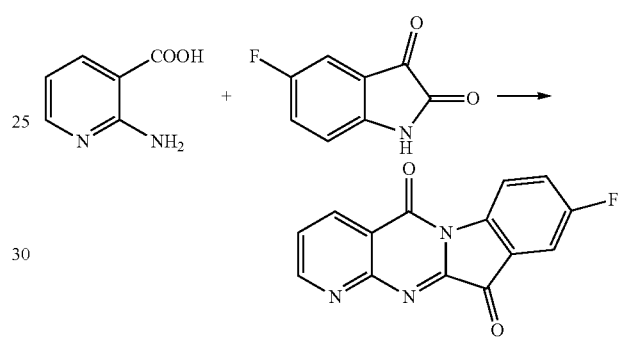

The procedure was the same as that of CY-1-1 of Example 1, except for replace isatin with 5-fluoroisatin. The product was a yellow solid with a yield of 51%. 41 NMR (400 MHz, DMSO-d$_6$) δ 9.07 (s, 1H), 8.69 (d, J=6.4 Hz, 1H), 8.44 (d, J=4.7 Hz, 1H), 7.83 (d, J=4.5 Hz, 1H), 7.75 (d, J=7.5 Hz, 2H). $^{13}$C NMR (101 MHz, DMSO-d$_6$) δ 181.85, 160.13, 158.53, 157.46, 156.72, 142.41, 136.83, 125.34, 124.62, 124.34, 119.54, 119.23, 112.48, 112.18.

Example 3

Compound CY-1-3: 9-(trifluoromethoxy)pyrido[2',3':4,5]pyrimido[1,2-c]indole-5,11-dione

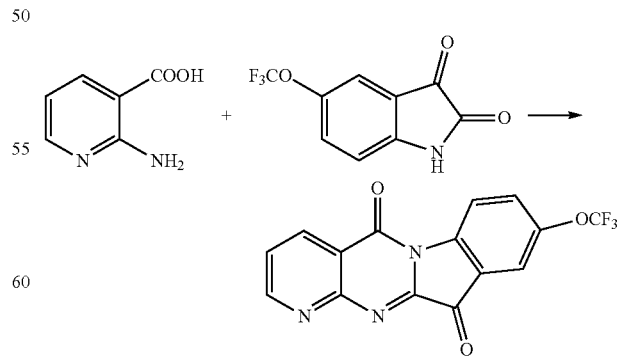

The procedure was the same as that of CY-1-1 of Example 1, except for replace isatin with 5-trifluoromethoxy-isatin. The product was a light yellow solid with a yield of 29%. $^1$H NMR (400 MHz, DMSO-d$_6$) δ 9.09 (d, J=3.7 Hz, 1H), 8.71 (d, J=7.7 Hz, 1H), 8.54 (d, J=8.7 Hz, 1H), 7.97 (s, 1H), 7.92 (d, J=8.7 Hz, 1H), 7.77 (dd, J=7.7, 4.6 Hz, 1H). $^{13}$C NMR (101 MHz, DMSO-d$_6$) δ 181.56, 158.48, 157.55, 156.84, 148.22, 146.96, 144.61, 136.89, 130.69, 125.40, 124.39, 121.75, 119.46, 119.19, 119.06, 118.38.

Example 4

Compound CY-1-4: 9-nitropyridine[2',3':4,5]pyrimido[1,2-c]indole-5,11-dione

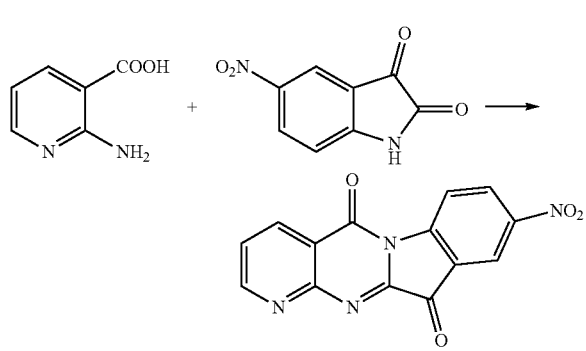

The procedure was the same as that of CY-1-1 of Example 1, except for replace isatin with 5-nitro-isatin. The product was a brown solid with a yield of 42%. $^1$H NMR (400 MHz, DMSO-d$_6$) δ 9.12 (d, J=3.9 Hz, 1H), 8.75 (d, J=8.0 Hz, 2H), 8.69-8.55 (m, 2H), 7.88-7.70 (m, 1H).

Example 5

Compound CY-1-5: 9-chloropyrido[2',3':4,5]pyrimido[1,2-c]indole-5,11-dione

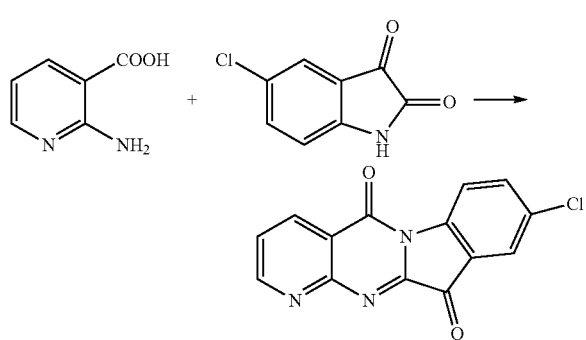

The procedure was the same as that of CY-1-1 of Example 1, except for replace isatin with 5-chloro-isatin. The product was a orange-yellow solid with a yield of 37%. $^1$H NMR (400 MHz, DMSO-d$_6$) δ 9.09 (dd, J=4.6, 2.0 Hz, 1H), 8.72 (dd, J=7.9, 2.0 Hz, 1H), 8.44 (d, J=8.6 Hz, 1H), 8.02 (d, J=2.2 Hz, 1H), 7.95 (dd, J=8.6, 2.3 Hz, 1H), 7.82-7.70 (m, 1H). $^{13}$C NMR (101 MHz, DMSO-d$_6$) δ 181.11, 157.96, 157.11, 156.28, 147.50, 144.11, 136.98, 136.36, 131.56, 124.86, 124.51, 123.89, 119.02, 118.46.

Example 6

Compound CY-1-6: 9-methoxypyrido[2',3':4,5]pyrimido[1,2-c]indole-5,11-dione

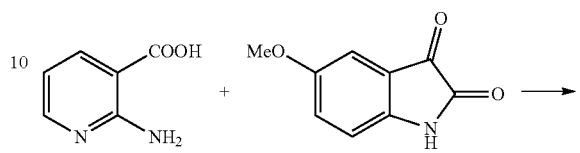

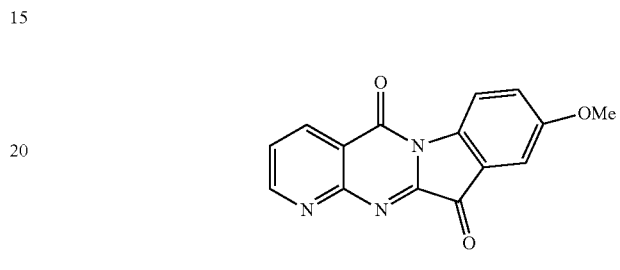

The procedure was the same as that of CY-1-1 of Example 1, except for replace isatin with 5-methoxy-isatin. The product was a yellow solid with a yield of 61%. $^1$H NMR (400 MHz, DMSO-d$_6$) δ 9.06 (dd, J=4.6, 2.0 Hz, 1H), 8.69 (dd, J=7.9, 1.9 Hz, 1H), 8.43-8.28 (m, 1H), 7.74 (dd, J=7.9, 4.6 Hz, 1H), 7.43 (dd, J=7.2, 2.6 Hz, 2H), 3.88 (s, 3H). $^{13}$C NMR (101 MHz, DMSO-d$_6$) δ 182.17, 158.21, 157.63, 157.16, 155.94, 147.93, 139.60, 136.15, 124.65, 123.79, 123.31, 119.27, 118.10, 108.76, 56.07.

Example 7

Compound CY-1-7: 9-methylpyrido[2',3':4,5]pyrimido[1,2-c]indole-5,11-dione

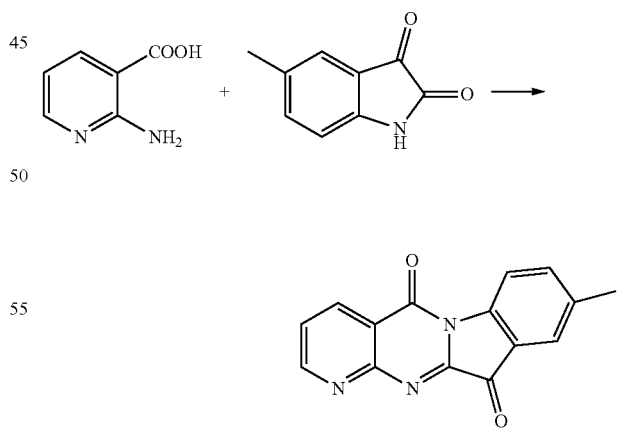

The procedure was the same as that of CY-1-1 of Example 1, except for replace isatin with 5-methy-isatin. The product was a yellow solid with a yield of 32%. $^1$H NMR (400 MHz, DMSO-d$_6$) δ 9.06 (d, J=4.2 Hz, 1H), 8.68 (d, J=7.8 Hz, 1H), 8.29 (d, J=8.1 Hz, 1H), 7.73 (dd, J=7.9, 4.2 Hz, 2H), 7.68 (d, J=8.1 Hz, 1H), 2.41 (s, 3H).

Example 8

Compound CY-1-8: pyrido[3',4':4,5]pyrimido[1,2-c]indole-5,11-dione

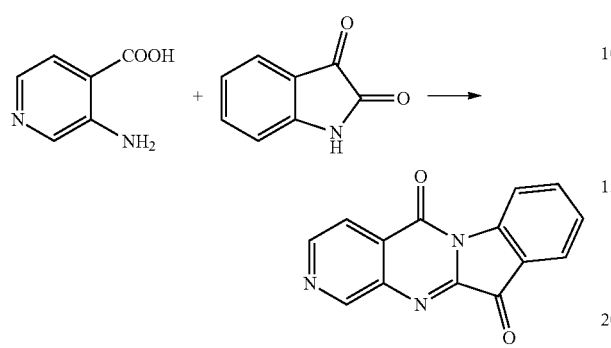

The procedure was the same as that of CY-1-1 of Example 1, except for replace 2-aminonicotinic acid with 3-aminoisonicotinic acid. The product was a yellow solid with a yield of 43%. $^1$H NMR (400 MHz, CD$_3$COOD) δ 9.74 (s, 1H), 9.01 (d, J=15.9 Hz, 2H), 8.55 (d, J=8.0 Hz, 1H), 8.00 (d, J=7.4 Hz, 1H), 7.91 (t, J=7.6 Hz, 1H), 7.57 (t, J=7.5 Hz, 1H). $^{13}$C NMR (101 MHz, CD$_3$COOD) δ 184.26, 156.83, 151.80, 148.25, 148.12, 146.82, 142.87, 142.20, 139.53, 132.11, 129.29, 128.30, 123.65, 120.90.

Example 9

Compound CY-1-9: 9-methoxypyrido[3',4':4,5]pyrimido[1,2-c]indole-5,11-dione

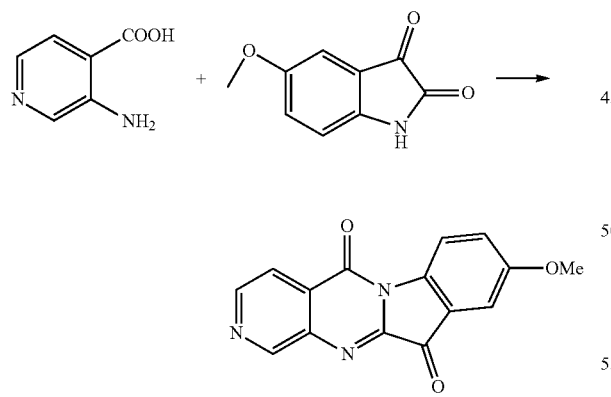

The procedure was the same as that of CY-1-1 of Example 1, except for replace 2-aminonicotinic acid with 3-aminoisonicotinic acid, and replace isatin with 5-methoxy-isatin. The product was a yellow solid with a yield of 33%. $^1$H NMR (400 MHz, CD$_3$COOD) δ 10.06-9.45 (m, 1H), 9.16-8.73 (m, 2H), 8.39 (t, J=21.2 Hz, 1H), 7.72-7.25 (m, 2H). $^{13}$C NMR (101 MHz, CD$_3$COOD) δ 182.06, 161.25, 154.76, 150.46, 150.06, 146.16, 144.42, 140.05, 137.18, 126.85, 126.32, 122.96, 120.36, 110.90, 55.62.

Example 10

Compound CY-1-10: 9-chloropyrido[3',4': 4,5]pyrimido[1,2-α]indole-5,11-dione

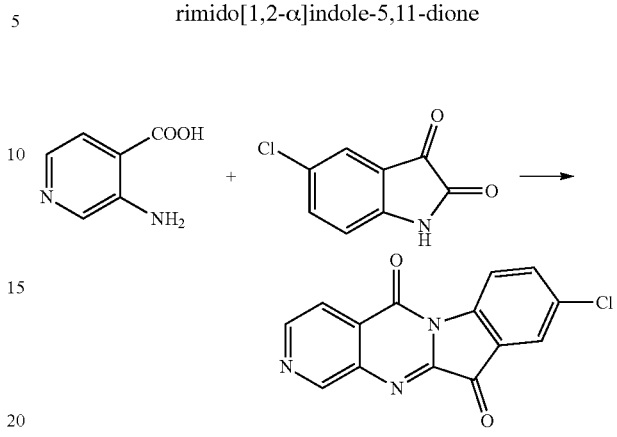

The procedure was the same as that of CY-1-1 of Example 1, except for replace 2-aminonicotinic acid with 3-aminoisonicotinic acid, and replace isatin with 5-chloro-isatin. The product was a yellow solid with a yield of 63%. $^1$H NMR (400 MHz, CD$_3$COOD) δ 9.51 (s, 1H), 8.82 (d, J=6.0 Hz, 1H), 8.76 (d, J=6.0 Hz, 1H), 8.29 (d, J=8.6 Hz, 1H), 7.72 (s, 1H), 7.69-7.52 (m, 1H). $^{13}$C NMR (101 MHz, CD$_3$COOD) δ 181.09, 155.04, 149.60, 146.28, 144.69, 144.09, 140.44, 140.08, 137.57, 137.19, 126.88, 126.37, 122.90, 119.78.

Example 11

Compound CY-1-11: 9-fluoropyrido[3',4':4,5]pyrimido[1,2-α]indole-5,11-dione

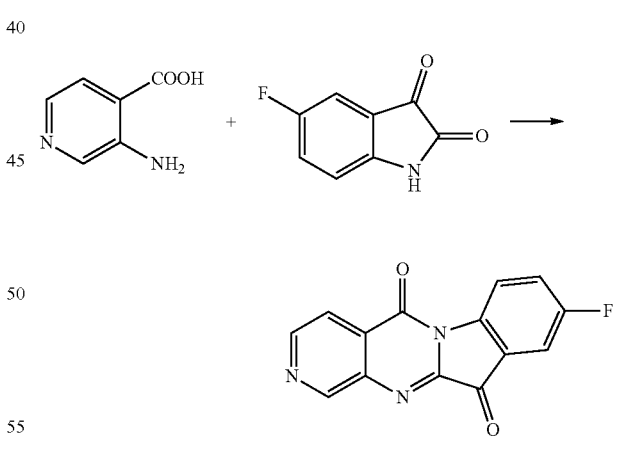

The procedure was the same as that of CY-1-1 of Example 1, except for replace 2-aminonicotinic acid with 3-aminoisonicotinic acid, and replace isatin with 5-fluoro-isatin. The product was a yellow solid with a yield of 67%. $^1$H NMR (400 MHz, CD$_3$COOD) δ 9.68 (s, 1H), 8.97 (dd, J=19.7, 6.1 Hz, 2H), 8.54 (dd, J=8.8, 3.7 Hz, 1H), 7.60 (dd, J=6.2, 2.5 Hz, 1H), 7.54 (td, J=8.6, 2.6 Hz, 1H). $^{13}$C NMR (101 MHz, CD$_3$COOD) δ 182.67, 156.28, 151.28, 147.40, 146.11, 143.84, 141.71, 139.01, 128.71, 128.39, 127.75, 124.91, 124.83, 122.34, 122.26, 115.34.

Example 12

Compound CY-1-12: 11-(hydroxyimino)pyrido[2',3': 4,5]pyrimido[1,2-α]indol-5(11H)-one

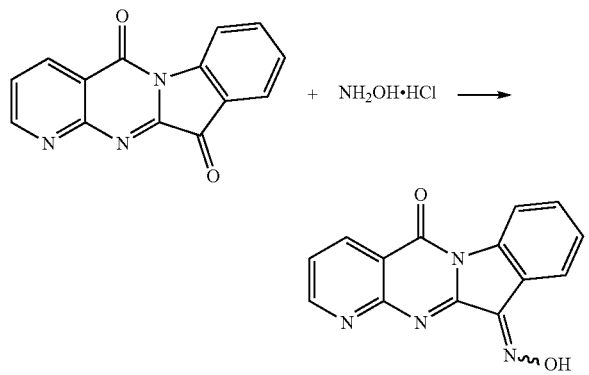

Compound CY-1-1 (1 mmol) and hydroxylamine hydrochloride (1 mmol) were dissolved in methanol (10 mL), pyridine (1 mmol) was added, and the mixture was heated to reflux overnight until the reaction was completed, and the solvent was evaporated to dryness, and then purified by column chromatography (dichloromethane: methanol=80:1) to furnish an orange-yellow solid with a yield of 69%. $^1$H NMR (400 MHz, DMSO-d$_6$) δ 14.01 (s, 1H), 9.02 (m, 1H), 8.71 (d, J=7.8 Hz, 1H), 8.45 (d, J=8.0 Hz, 1H), 8.35 (d, J=7.6 Hz, 1H), 7.71-7.60 (m, 2H), 7.47 (t, J=7.6 Hz, 1H). $^{13}$C NMR (101 MHz, DMSO-d$_6$) δ 159.07, 157.11, 155.34, 152.31, 144.70, 139.30, 137.46, 132.60, 127.75, 127.54, 123.31, 119.19, 117.90, 116.60.

Example 13

Compound CY-1-13: 9-chloro-11-(hydroxyimino) pyrido[2',3':4,5]pyrimido[1,2-α]indole-5(11H)-one

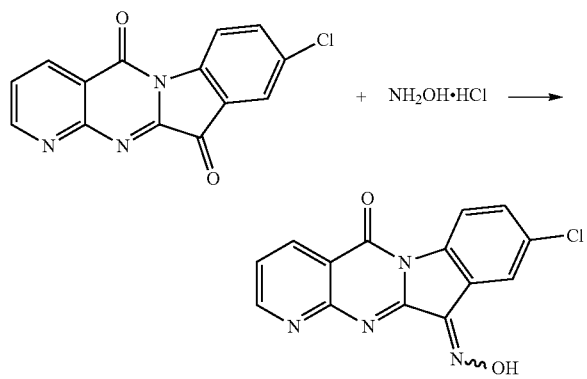

The procedure was the same as that of CY-1-12 of Example 12, except for replace Compound CY-1-1 with Compound CY-1-5. The product was a yellow solid with a yield of 56%. $^1$H NMR (400 MHz, DMSO-d$_6$) δ 14.16 (s, 1H), 9.03 (s, 1H), 8.63 (d, J=7.7 Hz, 1H), 8.37 (t, J=8.0 Hz, H), 8.32 (s, 1H), 7.79-7.48 (m, 2H). $^{13}$C NMR (101 MHz, DMSO-d$_6$) δ 159.17, 157.63, 156.32, 151.44, 143.93, 137.99, 136.47, 132.11, 131.24, 126.98, 123.36, 120.64, 118.03, 117.35.

Example 14

Compound CY-1-14: 11-(hydroxyimino)-9-methyl-pyrido[2',3': 4,5]pyrimido[1,2-α]indole-5 (11H)-one

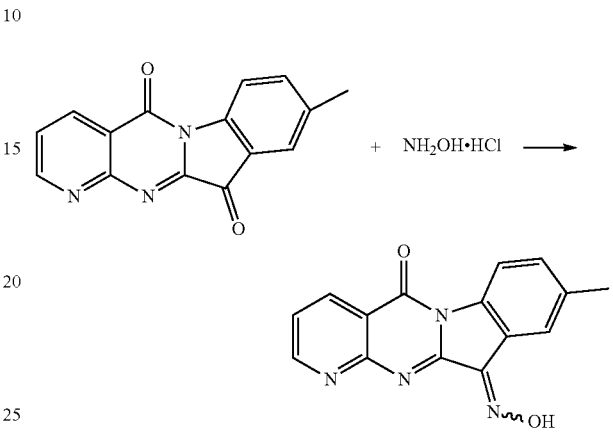

The procedure was the same as that of CY-1-12 of Example 12, except for replace Compound CY-1-1 with Compound CY-1-7. The product was a yellow solid with a yield of 71%. $^1$H NMR (400 MHz, DMSO-d$_6$) δ 13.31 (s, 1H), 8.99 (s, 1H), 8.61 (d, J=7.6 Hz, 1H), 8.30 (d, J=8.0 Hz, 1H), 8.15 (s, 1H), 7.61 (d, J=4.8 Hz, 1H), 7.41 (d, J=7.9 Hz, 1H), 2.38 (s, 4H). $^{13}$C NMR (101 MHz, DMSO-d$_6$) δ 159.03, 157.59, 156.13, 151.80, 144.68, 137.23, 136.89, 136.33, 132.84, 128.06, 123.13, 119.21, 117.57, 116.24, 21.04.

Example 15

Compound CY-1-15: 11-(hydroxyimino)-9-methoxypyrido[2',3':4,5]pyrimido[1,2-α]indole-5 (11H)-one

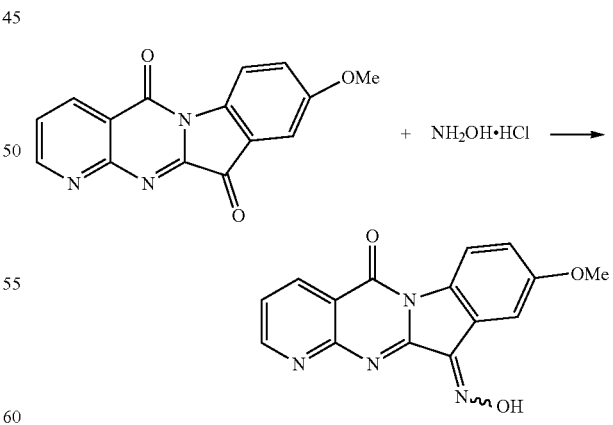

The procedure was the same as that of CY-1-12 of Example 12, except for replace Compound CY-1-1 with Compound CY-1-6. The product was a yellow solid with a yield of 48%. $^1$H NMR (400 MHz, DMSO-d$_6$) δ 13.92 (s, 1H), 9.52-8.78 (m, 1H), 8.61 (d, J=7.8 Hz, 1H), 8.33 (d, J=8.8 Hz, 1H), 7.84 (s, 1H), 7.60 (dd, J=7.7, 4.6 Hz, 1H), 7.17 (d, J=8.7 Hz, 1H), 3.82 (s, 3H). $^{13}$C NMR (101 MHz, DMSO-d$_6$) δ 158.73, 158.24, 157.62, 156.05, 151.66, 144.65, 136.36, 132.99, 123.07, 120.15, 117.62, 117.56, 117.48, 112.81, 55.99.

Example 16

Compound CY-1-16: 11-((2-(dimethylamino)ethoxy)imino)pyrido[2',3':4,5]pyrimido[1,2-α]indole-5(11H)-one

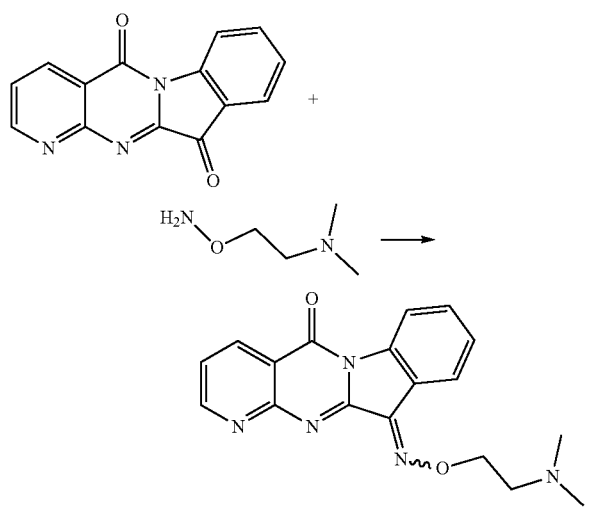

The procedure was the same as that of CY-1-12 of Example 12, except for replace hydroxylamine hydrochloride with N,N-dimethyl-2-aminooxyethylamine hydrochloride. The product was a yellow solid. $^{1}$H NMR (400 MHz, DMSO-d$_6$) δ 9.19-8.92 (m, 1H), 8.83-8.60 (m, 1H), 8.45 (m, 1H), 8.28 (d, J=7.6 Hz, 1H), 7.59 (m, 3H), 4.78-4.48 (m, 2H), 2.97-2.66 (m, 2H), 2.33 (s, 6H). $^{13}$C NMR (101 MHz, DMSO-d$_6$) δ 159.21, 157.63, 156.27, 151.01, 144.78, 140.08, 136.60, 133.43, 128.28, 127.21, 123.56, 118.82, 117.78, 116.62, 75.05, 57.54, 45.78.

Example 17

Compound CY-1-17: 11-((2-(dimethylamino)ethoxy)imino)-9-nitropyrido[2',3':4,5]pyrimido[1,2-α]indol-5(11H)-one

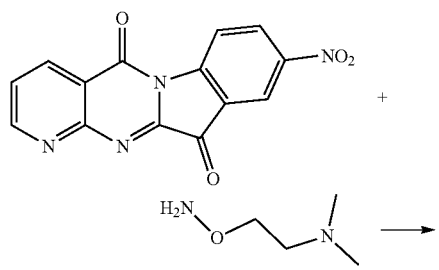

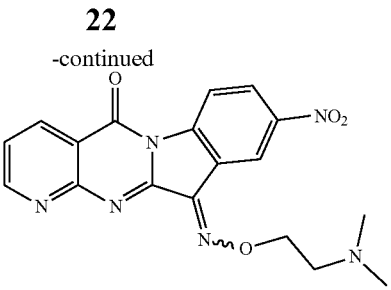

The procedure was the same as that of CY-1-12 of Example 12, except for replace hydroxylamine hydrochloride with N,N-dimethyl-2-aminooxyethylamine hydrochloride, and replace CY-1-1 with CY-1-4. The product was a yellow solid with a yield of 32%. 41 NMR (400 MHz, CDCl$_3$) δ 9.12 (s, 1H), 9.09-9.04 (m, 1H), 8.83-8.65 (m, 2H), 8.59-8.41 (m, 1H), 7.55 (dd, J=7.3, 4.9 Hz, 1H), 4.79 (t, J=5.5 Hz, 2H), 2.98 (t, J=10.9, 10.0 Hz, 2H), 2.36 (s, 6H).

Example 18

Compound CY-1-18: 9-chloro-11-((2-(dimethylamino)ethoxy)imino)pyrido[2',3':4,5]pyrimido[1,2-α]indol-5(11H)-one The procedure was the same as that of CY-1-12 of Example 12, except for replace hydroxylamine hydrochloride with N,N-dimethyl-2-aminooxyethylamine hydrochloride, and replace CY-1-1 with CY-1-5. The product was a yellow solid with a yield of 41%. $^{1}$H NMR (400 MHz, CDCl3) δ 9.03 (s, 1H), 8.70 (s, 1H), 8.58-8.46 (m, 1H), 8.26 (s, 1H), 7.59-7.43 (m, 2H), 4.65 (m, 2H), 2.89 (s, 2H), 2.31 (s, 6H). $^{13}$C NMR (101 MHz, CDCl3) δ 158.93, 157.47, 156.12, 150.59, 143.27, 137.66, 136.38, 132.73, 132.52, 128.09, 123.01, 119.98, 117.87, 117.36, 57.90, 45.77, 29.80.

Example 19

Compound CY-1-19: 11-((2-(dimethylamino)ethoxy)imino)-9-fluoropyrido[2',3':4,5]pyrimido[1,2-α]indol-5(11H)-one

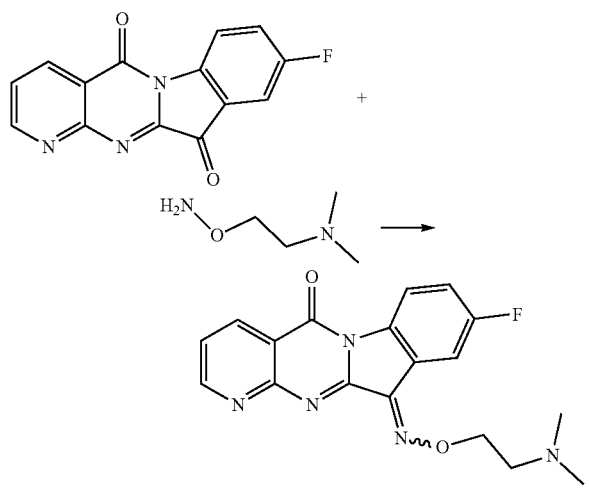

The procedure was the same as that of CY-1-12 of Example 12, except for replace hydroxylamine hydrochloride with N,N-dimethyl-2-aminooxyethylamine hydrochloride, and replace CY-1-1 with CY-1-2. The product was a yellow solid with a yield of 43%. $^1$H NMR (400 MHz, DMSO-d$_6$) δ 9.06-8.98 (m, 1H), 8.71-8.59 (m, 1H), 8.52-8.36 (m, 1H), 8.15 (dd, J=8.2, 2.5 Hz, 1H), 7.76-7.63 (m, 2H), 7.55 (ddd, J=27.5, 9.1, 2.6 Hz, 1H), 4.92 (s, 2H), 3.66 (s, 2H), 2.93 (s, 6H). $^{13}$C NMR (101 MHz, DMSO-d$_6$) δ 159.04, 156.49, 150.83, 136.85, 124.62, 123.90, 120.31, 120.01, 119.20, 118.66, 118.16, 117.88, 115.56, 108.50, 71.81, 55.72, 43.10.

Example 20

Compound CY-1-20: 9-chloro-11-((3-(dimethylamino)propoxy)imino)pyrido[2',3':4,5]pyrimido[1,2-α]indol-5(11H)-one

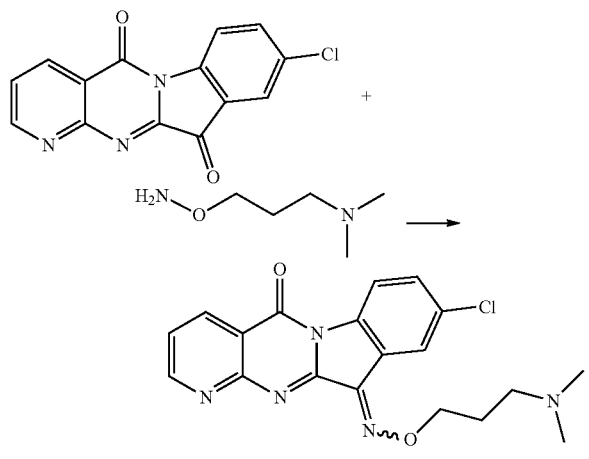

The procedure was the same as that of CY-1-12 of Example 12, except for replace hydroxylamine hydrochloride with N,N-dimethyl-2-aminooxyethylamine hydrochloride, and replace CY-1-1 with CY-1-5. The product was a yellow solid with a yield of 49%. $^1$H NMR (400 MHz, DMSO-d$_6$) δ 9.11-8.92 (m, 1H), 8.60 (dd, J=7.9, 1.7 Hz, 1H), 8.35 (d, J=8.6 Hz, 1H), 8.11 (d, J=1.7 Hz, 1H), 7.72 (dd, J=8.6, 2.1 Hz, 1H), 7.65 (dd, J=7.8, 4.6 Hz, 1H), 4.66 (t, J=5.9 Hz, 2H), 3.32-3.19 (m, 3H), 2.80 (s, 6H). $^{13}$C NMR (101 MHz, DMSO-d$_6$) δ 158.41, 156.85, 156.04, 150.09, 143.62, 138.01, 136.10, 132.73, 130.96, 127.02, 123.36, 119.63, 117.58, 117.16, 74.61, 53.63, 42.35, 24.24.

Example 21

Compound CY-1-21: 11-((2-hydroxyethoxy)imino)-9-nitropyrido[2',3':4,5]pyrimido[1,2-α]indol-5(11H)-one

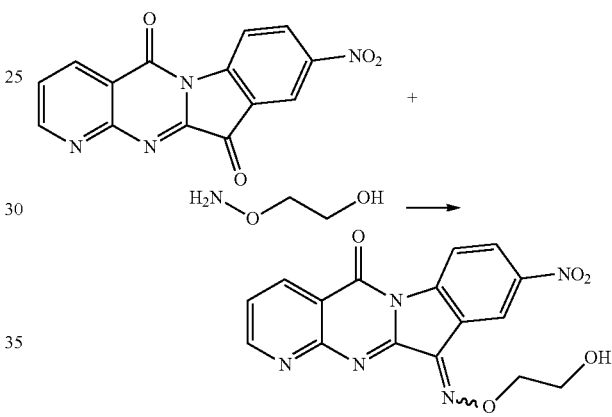

The procedure was the same as that of CY-1-12 of Example 12, except for replace hydroxylamine hydrochloride with 2-aminooxyethanol, and replace CY-1-1 with CY-1-4. The product was a light yellow solid with a yield of 48%. $^1$H NMR (400 MHz, DMSO-d$_6$) δ 9.02 (s, 1H), 8.89 (s, 1H), 8.72-8.41 (m, 3H), 7.66 (s, 1H), 4.99 (m, 1H), 4.65 (s, 2H), 3.88 (s, 2H). $^{13}$C NMR (101 MHz, DMSO-d$_6$) δ 159.29, 157.29, 156.73, 150.96, 145.79, 143.81, 143.47, 136.71, 129.26, 124.04, 122.71, 119.41, 117.67, 117.12, 80.33, 60.05.

Example 22

Compound CY-1-22: N,N-dimethyl-2-(9-nitro-5-oxopyrido[2',3':4,5]pyrimido[1,2-α]indol-11(5H)-ylidene)hydrazine-1-carbothioamide

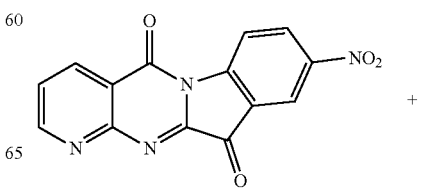

-continued

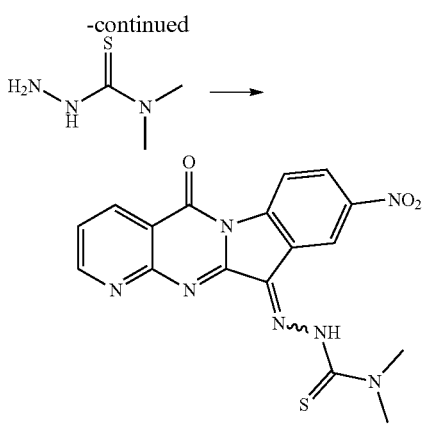

The procedure was the same as that of CY-1-12 of Example 12, except for replace hydroxylamine hydrochloride with N,N-dimethyl thiosemicarbazide, and replace CY-1-1 with CY-1-4. The product was a purple solid with a yield of 39%. $^1$H NMR (400 MHz, DMSO-d$_6$) δ 10.14-8.71 (m, 2H), 8.27 (m, 3H), 7.48 (m, 1H), 3.06 (m, 6H).

Example 23

Compound CY-1-23: 2-(9-nitro-5-oxopyrido[2',3':4,5]pyrimido[1,2-c]indol-11(5H)-ylidene)hydrazine-1-carboximidamide

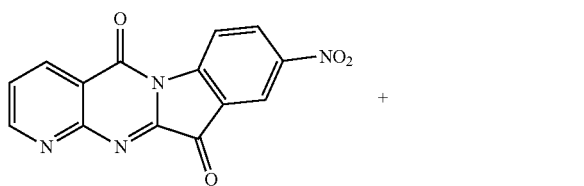

The procedure was the same as that of CY-1-12 of Example 12, except for replace hydroxylamine hydrochloride with aminoguanidine, and replace CY-1-1 with CY-1-4. The product was an orange solid with a yield of 21%. $^1$H NMR (400 MHz, CD$_3$COOD) δ 9.31 (d, J=7.9 Hz, 1H), 9.02 (d, J=5.7 Hz, 1H), 8.72 (d, J=1.7 Hz, 1H), 8.59 (s, 1H), 8.52 (d, J=8.9 Hz, 1H), 8.44-8.34 (m, 1H), 8.01 (d, J=1.7 Hz, 1H).

Example 24

Compound CY-1-24: (((9-nitro-5-oxopyrido[2',3':4,5]pyrimido[1,2-α]indol-11(5H)-ylidene)amino)oxy)sulfonic acid

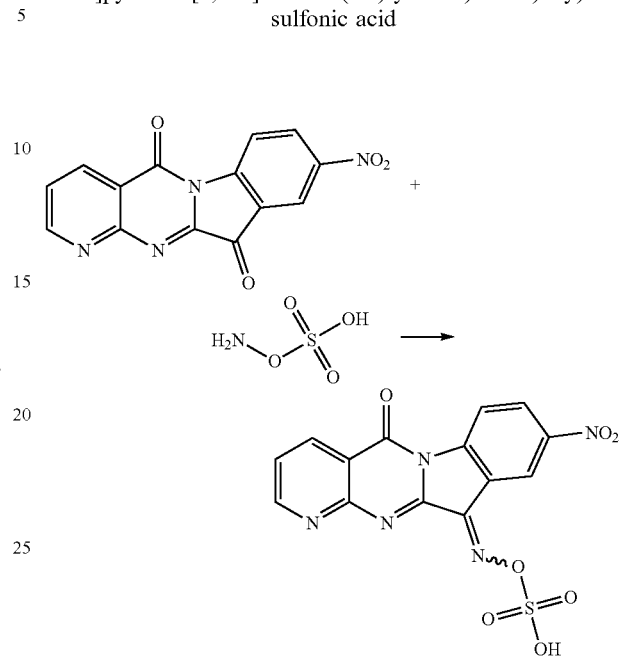

The procedure was the same as that of CY-1-12 of Example 12, except for replace hydroxylamine hydrochloride with sulfamic acid, and replace CY-1-1 with CY-1-4. The product was a white solid with a yield of 47%. $^1$H NMR (400 MHz, DMSO-d$_6$) δ 14.43 (s, 1H), 9.03 (dd, J=4.4, 1.7 Hz, 1H), 8.99 (d, J=2.3 Hz, 1H), 8.70-8.61 (m, 2H), 8.56 (dd, J=8.9, 2.4 Hz, 1H), 7.66 (dd, J=7.9, 4.6 Hz, 1H). $^{13}$C NMR (101 MHz, DMSO-d$_6$) δ 159.44, 157.55, 156.62, 151.63, 145.77, 143.55, 143.36, 136.69, 128.47, 123.66, 122.19, 119.53, 117.43, 117.05.

Example 25

Compound CY-1-25: 11-(methoxyimino)-9-nitropyrido[2',3': 4,5]pyrimido[1,2-α]indol-5 (11H)-one

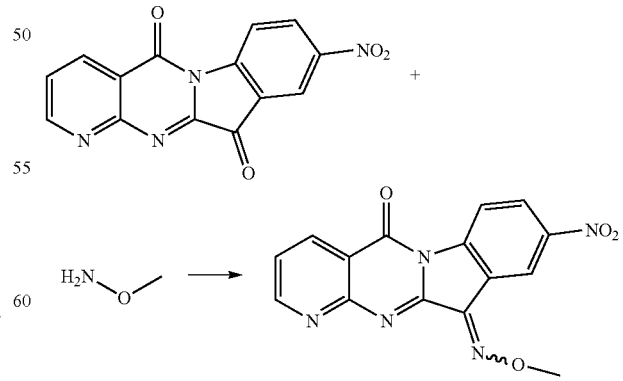

The procedure was the same as that of CY-1-12 of Example 12, except for replace hydroxylamine hydrochloride with O-methylhydroxylamine, and replace CY-1-1 with CY-1-4. The product was a light yellow solid with a yield of 28%. ¹H NMR (400 MHz, DMSO-d₆) δ 9.03 (dd, J=4.4, 1.8 Hz, 1H), 8.82 (s, 1H), 8.66 (dd, J=7.8, 1.6 Hz, 1H), 8.63-8.54 (m, 2H), 7.67 (dd, J=7.9, 4.6 Hz, 1H), 4.42 (s, 3H).

Example 26

Compound CY-1-26: 11-(ethoxyimino)-9-nitropyrido[2',3':4,5]pyrimido[1,2-α]indol-5(11H)-one

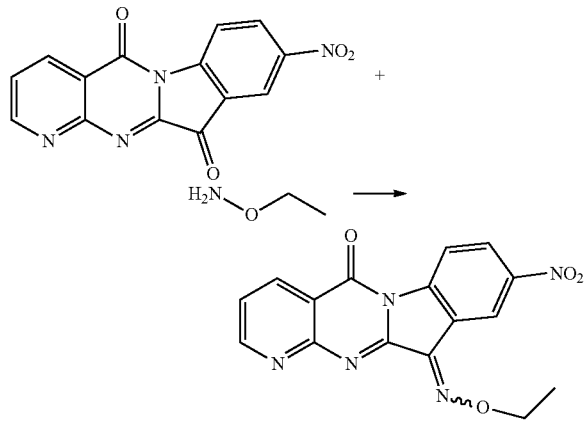

The procedure was the same as that of CY-1-12 of Example 12, except for replace hydroxylamine hydrochloride with O-ethylhydroxylamine, and replace CY-1-1 with CY-1-4. The product was a light yellow solid with a yield of 57%. ¹H NMR (400 MHz, DMSO-d₆) δ 9.07-9.02 (m, 1H), 8.85 (s, 1H), 8.67 (t, J=7.0 Hz, 1H), 8.65 (m, 2H), 7.68 (dd, J=7.8, 4.6 Hz, 1H), 4.68 (q, J=7.0 Hz, 2H), 1.50 (t, J=7.1 Hz, 3H). ¹³C NMR (101 MHz, DMSO-d₆) δ 59.22, 157.30, 156.68, 150.99, 145.79, 143.92, 143.31, 136.70, 129.23, 123.92, 122.39, 119.31, 117.60, 117.17, 74.28, 14.65.

Example 27

Compound CY-1-27: 11-((allyloxy)imino)-9-nitropyrido[2',3':4,5]pyrimido[1,2-α]indol-5(11H)-one

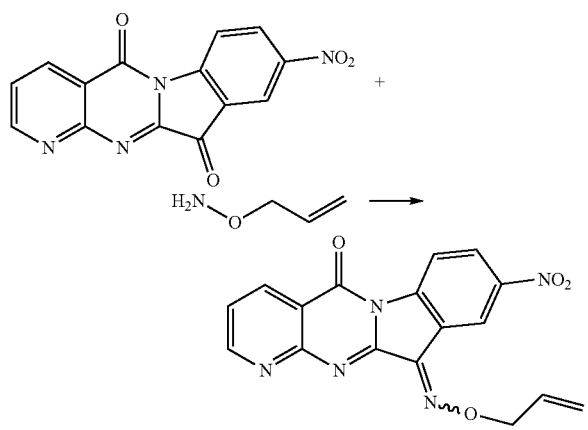

The procedure was the same as that of CY-1-12 of Example 12, except for replace hydroxylamine hydrochloride with O-allylhydroxylamine, and replace CY-1-1 with CY-1-4. The product was a light yellow solid with a yield of 32%. ¹H NMR (400 MHz, DMSO-d₆) δ 9.08-9.03 (m, 1H), 8.90 (d, J=1.9 Hz, 1H), 8.74-8.59 (m, 3H), 7.69 (dd, J=7.8, 4.6 Hz, 1H), 6.22 (m, 1H), 5.55 (d, J=17.2 Hz, 1H), 5.44 (d, J=10.7 Hz, 1H), 5.18 (d, J=5.6 Hz, 2H). ¹³C NMR (101 MHz, DMSO-d₆) δ 159.34, 157.27, 156.77, 151.03, 145.85, 144.18, 143.96, 136.47, 133.64, 129.20, 123.99, 122.44, 120.07, 119.54, 117.67, 117.04, 78.70.

Example 28

Compound CY-1-28: 11-((carboxymethoxyimino)-9-nitropyridine[2',3': 4,5]pyrimido[1,2-α]indole-5(11H)-one

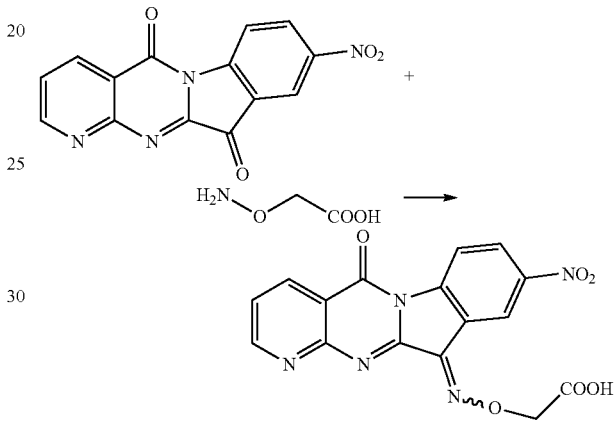

The procedure was the same as that of CY-1-12 of Example 12, except for replace hydroxylamine hydrochloride with 3-aminooxyacetic acid, and replace CY-1-1 with CY-1-4. The product was a white solid with a yield of 33%. ¹NMR (400 MHz, DMSO-d₆) δ 9.11-8.92 (m, 2H), 8.63 (m, 3H), 7.74-7.62 (m, 1H), 3.79 (s, 2H). ¹³C NMR (101 MHz, DMSO-d₆) δ 170.31, 169.20, 159.29, 157.45, 156.73, 150.82, 145.84, 144.76, 144.54, 144.30, 144.27, 136.76, 129.83, 129.69, 124.11, 123.13, 119.30, 117.89, 117.29, 73.79.

Example 29

Compound CY-1-29: 2-(9-nitro-5-oxopyrido[2',3':4,5]pyrimido[1,2-c]indol-11(5H)-ylidene)hydrazine-1-carbothioamide

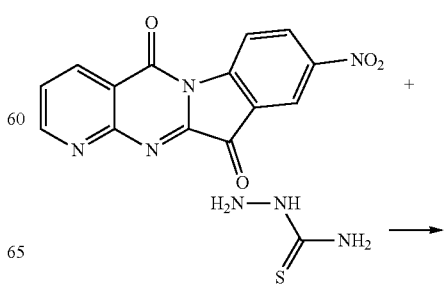

29

-continued

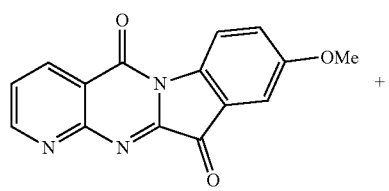

The procedure was the same as that of CY-1-12 of Example 12, except for replace hydroxylamine hydrochloride with thiosemicarbazide, and replace CY-1-1 with CY-1-4. The product was a red solid with a yield of 29%. $^1$H NMR (400 MHz, DMSO-$d_6$) δ 9.19-8.98 (m, 1H), 8.84-8.64 (m, 2H), 8.63-8.47 (m, 2H), 7.89-7.65 (m, 1H), 4.56 (m, 1H).

Example 30

Compound CY-1-30: 2-(9-methoxy-5-oxopyrido[2', 3':4,5]pyrimido[1,2-α]indol-11(5H)-ylidene)-N,N-dimethyl-hydrazine-1-carbothioamide The procedure was the same as that of CY-1-12 of Example 12, except for replace hydroxylamine hydrochloride with N,N-dimethyl thiosemicarbazide, and replace CY-1-1 with CY-1-6. The product was a red solid with a yield of 52%. $^1$H NMR (400 MHz, CD$_3$COOD) δ 9.22 (t, J=10.8 Hz, 1H), 8.99-8.72 (m, 1H), 8.21-8.03 (m, 1H), 7.99-7.74 (m, 1H), 7.26 (m, 1H), 7.16-6.83 (m, 1H), 4.00-2.95 (m, 9H).

30

Example 31

Compound CY-1-31: pyrido[2,3-D]pyrido[3 ',4': 4,5]pyrrolo[1,2-α]pyrimidine-5,11-dione

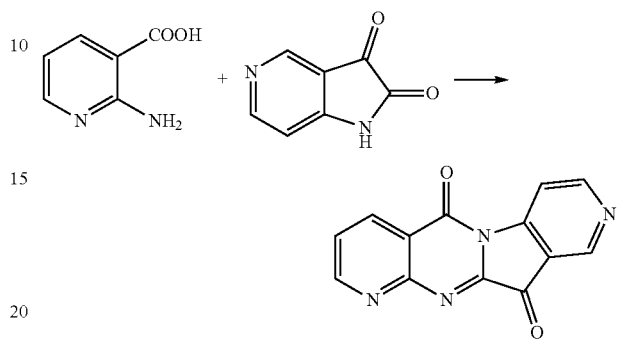

The procedure was the same as that of CY-1-1 of Example 1, except for replace isatin with 5-aza-isatin. The product was a yellow solid with a yield of 41%. HR-ESI-MS: Calcd for C$_{13}$H$_6$N$_4$O$_2$ [M+H]+: 251.05032, found: 251.04989.

Example 32

Compound LDB-1-1: 2-(9-chloro-5-oxopyrido[2',3': 4,5]pyrimido[1,2-α]indol-11 (5H)-ylidene)hydrazine-1-carboximidamide

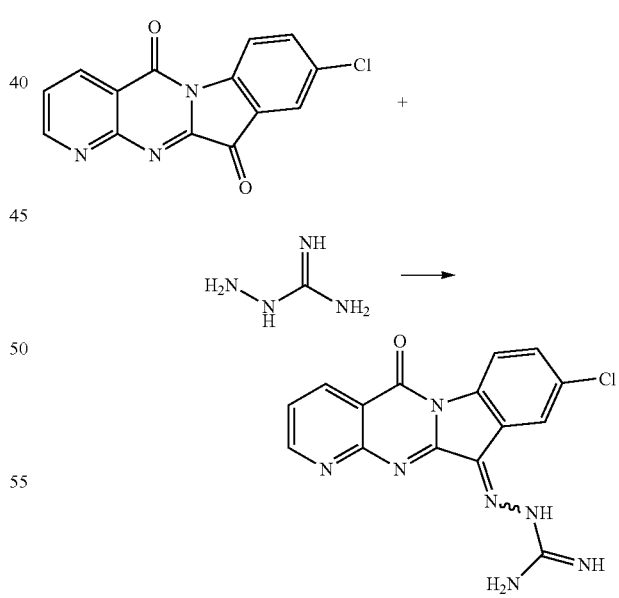

The procedure was the same as that of CY-1-12 of Example 12, except for replace hydroxylamine hydrochloride with aminoguanidine, and replace CY-1-1 with CY-1-5. The product was an orange-yellow solid with a yield of 43%. 采 HR-ESI-MS: Calcd for C$_{15}$H$_{10}$ClN$_7$O [1\4+H]+: 340.10, found: 340.10.

Example 33

Compound LDB-1-2: 2-(9-chloro-5-oxopyrido[2',3': 4,5]pyrimido[1,2-c]indol-11(5H)-ylidene)hydrazine-1-carbothioamide The procedure was the same as that of CY-1-12 of Example 12, except for replace hydroxylamine hydrochloride with thiosemicarbazide, and replace CY-1-1 with CY-1-5. The product was a yellow solid with a yield of 65%. ¹H NMR (400 MHz, DMSO-d6) δ 12.85 (s, 1H), 9.30 (s, 1H), 9.07 (s, 2H), 8.73 (s, 1H), 8.39 (s, 1H), 8.23 (s, 1H), 7.73 (s, 1H), 7.70 (s, 1H).

Example 34

Compound LDB-1-3: 2-(9-(trifluoromethoxy)-5-oxopyrido[2',3':4,5]pyrimido[1,2-c]indol-11(5H)-ylidene)hydrazine-1-carboximidamide

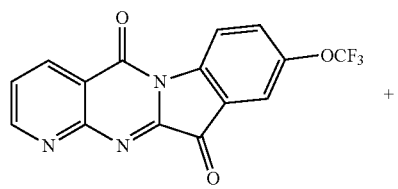
+
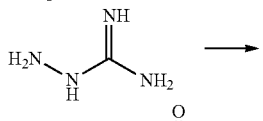
→
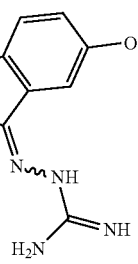

The procedure was the same as that of CY-1-12 of Example 12, except for replace hydroxylamine hydrochloride with aminoguanidine, and replace CY-1-1 with CY-1-3. The product was an orange-yellow solid with a yield of 49%. HR-ESI-MS: Calcd for $C_{16}H_{10}F_3N_7O_2$ [M+H]+: 390.10, found: 390.10.

Example 35

Compound LDB-1-4: 2-(9-(trifluoromethoxy)-5-oxopyrido[2',3':4,5]pyrimido[1,2-c]indol-11(5H)-ylidene)hydrazine-1-carbothioamide

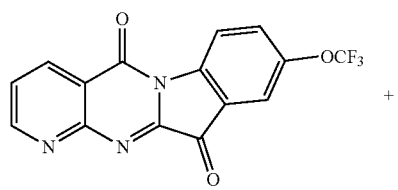
+
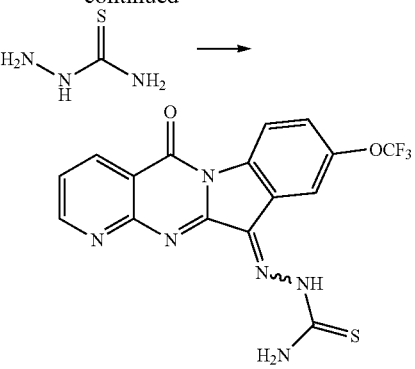

The procedure was the same as that of CY-1-12 of Example 12, except for replace hydroxylamine hydrochloride with thiosemicarbazide, and replace CY-1-1 with CY-1-3. The product was a yellow solid with a yield of 56%. 41 NMR (400 MHz, DMSO-d6) δ 12.87 (s, 1H), 9.33 (s, 1H), 9.15-9.04 (m, 2H), 8.74 (dd, J=7.9, 2.2 Hz, 1H), 8.46 (d, J=8.8 Hz, 1H), 8.16 (s, 1H), 7.74 (dd, J=7.7, 4.9 Hz, 1H), 7.64 (d, J=8.9 Hz, 1H). ¹³C NMR (101 MHz, DMSO) δ 114.07, 117.39, 117.74, 123.67, 123.85, 125.39, 129.35, 136.30, 137.56, 146.54, 148.03, 156.03, 156.26, 158.14, 178.89.

Example 36

Compound LDB-1-5: 2-(9-chloro-5-oxopyrido[3',4': 4,5]pyrimido[1,2-c]indol-11(5H)-ylidene)hydrazine-1-carboximidamide

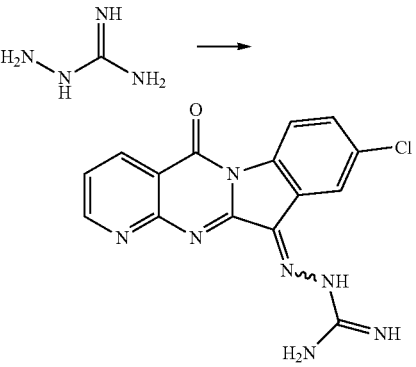

The procedure was the same as that of CY-1-12 of Example 12, except for replace hydroxylamine hydrochloride with aminoguanidine, and replace CY-1-1 with CY-1-10. The product was an orange solid with a yield of 52%. ¹H NMR (400 MHz, DMSO-d6) δ 12.84 (s, 1H), 9.73 (s, 1H), 9.34 (s, 1H), 8.85 (d, J=5.0 Hz, 1H), 8.60 (s, 2H), 8.34 (d, J=8.6 Hz, 1H), 8.25 (s, 1H), 8.16 (d, J=4.9 Hz, 1H), 7.72 (d, J=8.6 Hz, 1H). ¹³C NMR (101 MHz, DMSO) δ 117.95, 118.84, 121.70, 124.73, 127.09, 131.34, 131.51, 134.54, 138.00, 140.56, 146.18, 148.43, 151.37, 155.71, 156.76.

Example 37

Compound LDB-1-6: 2-(9-chloro-5-oxopyrido[3',4':4,5]pyrimido[1,2-c]indol-11(5H)-ylidene)hydrazine-1-carbothioamide

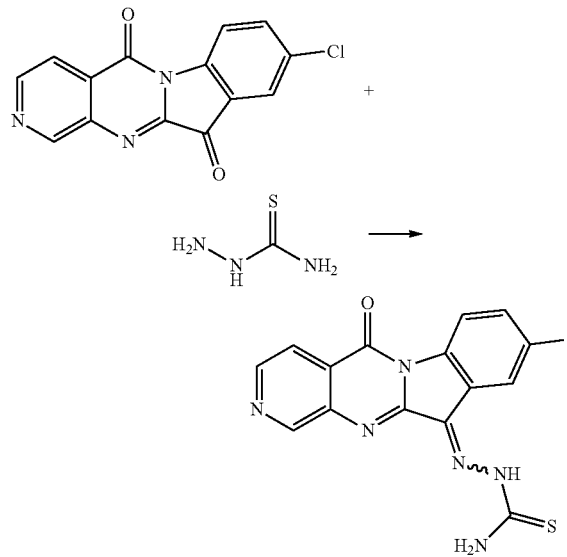

The procedure was the same as that of CY-1-12 of Example 12, except for replace hydroxylamine hydrochloride with thiosemicarbazide, and replace CY-1-1 with CY-1-10. The product was a yellow solid with a yield of 47%. $^1$H NMR (400 MHz, DMSO-d6) δ 12.54 (s, 1H), 9.26 (s, 1H), 9.10 (d, J=2.4 Hz, 1H), 8.99 (s, 1H), 8.82 (d, J=4.8 Hz, 1H), 8.27 (d, J=8.5 Hz, 1H), 8.12 (s, 2H), 7.59 (d, J=8.5 Hz, 1H). $^{13}$C NMR (101 MHz, DMSO) δ 117.80, 118.99, 120.96, 125.20, 126.76, 128.62, 130.46, 131.38, 137.20, 140.46, 146.46, 148.14, 150.19, 156.67, 178.72.

Biological Activity Test Example

Indoleamine-2,3-Dioxygenase 1 Inhibitory Activity

Experimental method: IDO-1 can oxidatively cleave the indole ring of tryptophan to form N-formylkynurenine. Referring to the method in the literature (Eddy W. Yue, et al. J. Med. Chem. 2009, 52, 7364-7367), 20 nM IDO-1, 2 mM D-tryptophan, 20 mM ascorbic acid, 3.5M methyl blue and 0.2 mg/mL antioxidant enzyme were sequentially added to 50 mM potassium phosphate buffer at room temperature. Due to the formation of N-formylkynurenine, the reaction rate was recorded by the increasing absorbance of the solution at 321 nm. IC$_{50}$ values were calculated using Prism GraphPad software. The compound INCB024360 developed by Incyte Pharmaceutical Company of the United States was as a positive control drug, and the experimental results are as follows:

TABLE 2

IDO-1 inhibitory activity of compounds (IC$_{50}$, μM)

| Compounds No. | IC$_{50}$ (μM) |
|---|---|
| CY-1-1 | +++ |
| CY-1-2 | ++++ |
| CY-1-3 | ++++ |
| CY-1-4 | ++++ |
| CY-1-5 | ++++ |
| CY-1-6 | +++ |
| CY-1-7 | +++ |
| CY-1-8 | +++ |
| CY-1-9 | ++ |
| CY-1-10 | +++ |
| CY-1-11 | +++ |
| CY-1-12 | ++ |
| CY-1-13 | +++ |
| CY-1-14 | ++ |
| CY-1-15 | ++ |
| INCB024360 | +++/++++ |
| CY-1-16 | +++ |
| CY-1-17 | ++++ |
| CY-1-18 | +++ |
| CY-1-19 | +++ |
| CY-1-20 | ++ |
| CY-1-21 | +++ |
| CY-1-22 | ++++ |
| CY-1-23 | ++++ |
| CY-1-24 | +++ |
| CY-1-25 | +++ |
| CY-1-26 | ++ |
| CY-1-27 | ++ |
| CY-1-28 | +++ |
| CY-1-29 | ++++ |
| CY-1-30 | ++ |
| CY-1-31 | ++++ |

Notes:
++++ = 0.001-0.10 μM;
+++ = 0.11-1.0 μM;
++ = 1.1-10 μM.

Tryptophan-2,3-Dioxygenase Inhibitory Activity

Experimental method: TDO can oxidatively cleave the indole ring of tryptophan to form N-formylkynurenine. Referring to the method in the reference (Eddy W. Yue, et al. J. Med. Chem. 2009, 52, 7364-7367), a detection buffer containing 50 nM TDO, 10μM inhibitor, 200μM tryptophan, and the like were sequentially added thereto at room temperature. Due to the formation of N-formylkynurenine, the reaction rate was recorded by the increasing absorbance of the solution at 321 nm. IC$_{50}$ values were calculated using Prism GraphPad software. The experimental results of the enzyme inhibition rate at the concentration of compound 10μM are as follows:

TABLE 3

Inhibitory activity of compounds at 10 μM for TDO

| Compounds No. | Inhibition rate (%) |
|---|---|
| CY-1-1 | — |
| CY-1-2 | 44 |
| CY-1-3 | 16 |
| CY-1-4 | 97 |
| CY-1-5 | 35 |
| CY-1-6 | — |
| CY-1-7 | — |
| CY-1-8 | — |
| CY-1-9 | — |
| CY-1-10 | 8 |
| CY-1-11 | — |
| CY-1-12 | — |
| CY-1-13 | 6 |
| CY-1-14 | — |

TABLE 3-continued

Inhibitory activity of compounds at 10 μM for TDO

| Compounds No. | Inhibition rate (%) |
| --- | --- |
| CY-1-15 | — |
| CY-1-16 | — |
| CY-1-17 | 64 |
| CY-1-18 | — |
| CY-1-19 | — |
| CY-1-20 | — |
| CY-1-21 | — |
| CY-1-22 | — |
| CY-1-23 | 86 |
| CY-1-24 | — |
| CY-1-25 | — |
| CY-1-26 | — |
| CY-1-27 | — |
| CY-1-28 | — |
| CY-1-29 | 93 |
| CY-1-30 | — |
| CY-1-31 | — |

Noting:
— means that testing has not yet been done.

Experiment of Reducing Kynurenine Content in Venous Blood of Rats

The decrease of kynurenine concentration in venous blood of rats can reflect the inhibitory activity of the compound on IDO1 in vivo. Three male rats weighing approximately 300 g were randomly assigned to each group, and one-time intragastric administration of CY-1-4, CY-1-10, CY-1-17 fumarate, CY-1-26 hydrochloride and CY-1-30 for 50 mg/Kg. 120-150 μL of blood was collected from the rat's inner canthus at eight time points of 0, 0.5, 1, 2, 4, 8, 12, 24 hours, and centrifuged at 3000 rpm for 10 min, and taken the supernatant to obtain serum. The kynurenine concentrations in serum at different time points were determined by kynurenine ELISA test kit. The average kynurenine concentrations in vivo of three rats in each group was taken.

The results show that the test compounds show varying degrees of activity in reducing kynurenine concentration with reduction of 18-56%.

In vivo anti-tumor experiment:
CY-1-17 fumarate inhibits Lewis lung cancer in mice experiment The in vivo efficacy of the test compound was tested by C57BL/6J mice bearing Lewis lung cancer, and the intraperitoneal administration route (20 mg/Kg) was used, and cyclophosphamide (20 mg/Kg) was used as positive controls. The observation and measurement were started on the day of the first administration, and the relevant indicators were recorded. The tumor-bearing mice were sacrificed at the end of the experiment, and the tumor pieces were dissected and weighed. The tumor-bearing mice were administered intraperitoneally for 11 days. The body weight of the animals in the drug-administered group was slightly slower than that of the negative control group. Animals are in good condition and no obvious side effects have been observed. After 11 days of continuous intraperitoneal injection of tumor-bearing mice, the animals were euthanized, the subcutaneous tumors were dissected, weighed, photographed, and the animals were dissected for gross observation. The tumor weight of the animals in the administration group was significantly lower than that of the negative control group. The inhibition rate of cyclophosphamide was 29.9%, and the inhibition rate of CY-1-17 (20 mg/kg) was 51.8%. The dissected mice were observed in general, and no obvious tumor metastasis was observed.

CY-1-26 hydrochloride inhibits melanoma in mice experiment (1) Experimental method The in vivo efficacy of compound was tested with C57BL/6J mice bearing melanoma B16. The intragastric administration was 20 mg/kg, and 1-MT was a positive control (200 mg/kg), which was once daily. The observation and measurement were started on the day of the first administration, and the relevant indicators were recorded. The tumor-bearing mice were sacrificed at the end of the experiment, and the tumor pieces were dissected and weighed.

(2) Effect on body weight of tumor-bearing mice

The tumor-bearing mice were administered by continuous intragastric administration for 10 days. The body weight of the animals in the drug-administered group was slightly slower than that of the negative control group. The animals were in good condition and no obvious side effects were observed.

(3) Effect of tumor growth on tumor-bearing mice

After 10 days of administration, the animals were euthanized, the subcutaneous tumors were dissected, weighed, and the animals were dissected for gross observation. The tumor weight of the animals in the administration group was lower than that of the negative control group, and the tumor inhibition rate of 1-MT was 26.3%, and the tumor inhibition rate of CY-1-26 was 33.0%.

Repeated verification of CY-1-26 hydrochloride inhibiting melanoma in mice experiment (1) Experimental method The in vivo efficacy of compound was tested in three groups (6 in each group) of C57BL/6J mice bearing melanoma B16. CY-1-26 hydrochloride was intragastrically administered at 20 mg/kg (suspended in 0.5% sodium carboxymethyl cellulose solution), and 1-MT was a positive control (200 mg/kg, suspended in 0.5% sodium carboxymethyl cellulose solution), the blank control was 0.5% sodium carboxymethyl cellulose solution, all once daily dose. On the day of the first dose, the relevant indicators were observed, measured and recorded. At the end of the experiment, the tumor-bearing mice were sacrificed and the tumor pieces were dissected and weighed.

(2) Effect on body weight of tumor-bearing mice

The tumor-bearing mice were administered by continuous intragastric administration for 14 days. The body weight of the animals in the drug-administered group was slightly slower than that of the negative control group. The animals were in good condition and no obvious side effects were observed.

(3) Effect of tumor growth on tumor-bearing mice

After 14 days of administration, the animals were euthanized, the subcutaneous tumors were dissected, weighed, and the animals were dissected for gross observation. The tumor weight of the animals in the administration group was lower than that of the negative control group, and the tumor inhibition rate of CY-1-26 hydrochloride was 46.0%, significantly better than 1-MT.

In summary, the embodiment of the present invention introduces a nitrogen atom into a specific position of the tryptanthrin structure, and the obtained new derivatives have an unexpected improvement effect on the inhibitory activity against enzyme IDO1, and exhibit a strong inhibitory activity against TDO.

The above are only examples of the principles of the embodiment of the present application, and are not intended to limit the scope of the present application. Therefore, any modifications, equivalent substitutions, improvements, etc., shall be included in the scope of this application within the spirit and principles of this application.

INDUSTRIAL APPLICABILITY

The aza-tryptanthrin derivatives of the present application have inhibitory effects of IDO1 and/or TDO, which are key enzymes for the metabolism of tryptophan along the kynurenine pathway, and can be used as drugs for diseases with pathological features of IDO1 and/or TDO-mediated tryptophan metabolism (including but not limited to tumors, autoimmune diseases, infectious diseases, alzheimer's disease, depression, anxiety).

What we claim is:

1. An inhibitor for indoleamine-2,3-dioxygenase 1 or tryptophan-2,3-dioxygenase, wherein the inhibitor comprises an aza-tryptanthrin derivative, and the derivative is represented by Formula (II), or geometric isomers, tautomers, isotopic labels, hydrates, solvates, metabolites, pharmaceutically acceptable salt or prodrug thereof:

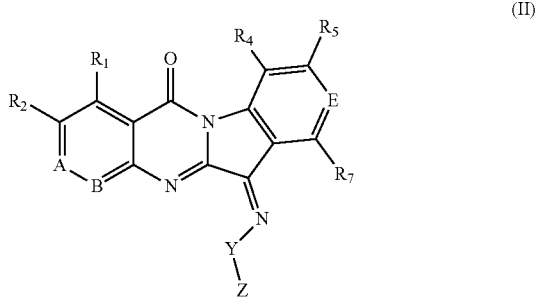

(II)

wherein, in the Formula (II),
one of A and B is N and the other is C—$R_3$;
E is N or —C—$R_6$;
Y is —O—, and Z is hydrogen, an unsubstituted or substituted C1-C4 alkyl group, an unsubstituted or substituted C2-C4 alkenyl group, an unsubstituted or substituted C2-C4 alkynyl group, a carboxymethyl group —$CH_2C(=O)OH$, a sulfonyl group —$S(=O)_2$ OH, or a phosphoryl group —$P(=O)(OH)_2$; and alternatively, Y is —N(H)—, and Z is hydrogen, —C(=S)—N($R_8$)($R_9$), —C(=O)—N($R_8$)($R_9$), or —C(=N)—N($R_8$)($R_9$);
$R_1$ to $R_7$ are each independently selected from hydrogen, an unsubstituted or substituted C1-C4 alkyl group, an unsubstituted or substituted C1-C4 alkoxy group, halogen, a nitro group, a cyano group, a methyl sulfonyl group or a hydroxyl group;
$R_8$ and $R_9$ are each independently selected from hydrogen or an unsubstituted C1-C4 alkyl group;
with the provision that when B is N, and A is —CH, and Y is —O—, and Z is hydrogen, and E is —C—R6, R6 is not hydrogen.

2. The inhibitor of claim 1, wherein, in the derivative, A is N and B is —CH, or B is N and A is —CH.

3. The inhibitor of claim 1, wherein, the derivative is selected from the following compounds:
9-chloro-11-(hydroxyimino)pyrido[2',3':4,5]pyrimido[1,2-α]indol-5(11H)-one;
11-(hydroxyimino)-9-methylpyrido[2',3':4,5]pyrimido[1,2-α]indole-5(11H)-one;
11-(hydroxyimino)-9-methoxypyrido[2',3':4,5]pyrimido[1,2-α]indole-5(11H)-one;
11-((2-(dimethylamino)ethoxy)imino)pyrido[2',3':4,5]pyrimido[1,2-α]indole-5(11H)-one;
11-((2-(dimethylamino)ethoxy)imino)-9-nitropyrido[2',3':4,5]pyrimido[1,2-α]indol-5(11H)-one;
9-chloro-11-((2-(dimethylamino)ethoxy)imino)pyrido[2',3':4,5]pyrimido[1,2-α]indol-5(11H)-one;
11-((2-(dimethylamino)ethoxy)imino)-9-fluoropyrido[2',3':4,5]pyrimido[1,2-α]indol-5(11H)-one;
9-chloro-11-((3-(dimethylamino)propoxy)imino)pyrido[2',3':4,5]pyrimido[1,2-α]indol-5(11H)-one
11-((2-hydroxyethoxy)imino)-9-nitropyrido[2',3':4,5]pyrimido[1,2-α]indol-5(11H)-one;
N,N-dimethyl-2-(9-nitro-5-oxopyrido[2',3':4,5]pyrimido[1,2-α]indol-11(5H)-ylidene)hydrazine-1-carbothioamide;
2-(9-nitro-5-oxopyrido[2',3':4,5]pyrimido[1,2-α]indol-11(5H)-ylidene)hydrazine-1-carboximidamide;
(((9-methyl-5-oxopyrido[2',3':4,5]pyrimido[1,2-α]indol-11(5H)-ylidene)amino)oxy) sulfonic acid;
11-(methoxyimino)-9-nitropyrido[2',3':4,5]pyrimido[1,2-α]indol-5(11H)-one;
11-(ethoxyimino)-9-nitropyrido[2',3':4,5]pyrimido[1,2-α]indol-5(11H)-one;
11-((allyloxy)imino)-9-nitropyrido[2',3':4,5]pyrimido[1,2-α]indol-5(11H)-one;
11-((carboxymethoxyimino)-9-nitropyridine[2',3':4,5]pyrimido[1,2-α]indole-5(11H)-one;
2-(9-nitro-5-oxopyrido[2',3':4,5]pyrimido[1,2-α]indol-11(5H)-ylidene)hydrazine-1-carbothioamide;
2-(9-methoxy-5-oxopyrido[2',3':4,5]pyrimido[1,2-α]indol-11(5H)-ylidene)-N,N-dimethyl-hydrazine-1-carbothioamide;
2-(9-chloro-5-oxopyrido[2',3':4,5]pyrimido[1,2-α]indol-11(5H)-ylidene)hydrazine-1-carboximidamide;
2-(9-chloro-5-oxopyrido[2',3':4,5]pyrimido[1,2-α]indol-11(5H)-ylidene)hydrazine-1-carbothioamide;
2-(9-(trifluoromethoxy)-5-oxopyrido[2',3':4,5]pyrimido[1,2-α]indol-11(5H)-ylidene)hydrazine-1-carboximidamide;
2-(9-(trifluoromethoxy)-5-oxopyrido[2',3':4,5]pyrimido[1,2-α]indol-11(5H)-ylidene)hydrazine-1-carbothioamide;
2-(9-chloro-5-oxopyrido[3',4':4,5]pyrimido[1,2-α]indol-11(5H)-ylidene)hydrazine-1-carboximidamide; and
2-(9-chloro-5-oxopyrido[3',4':4,5]pyrimido[1,2-α]indol-11(5H)-ylidene)hydrazine-1-carbothioamide.

4. The inhibitor of claim 1, wherein the inhibitor is capable of being used in the treatment of a disease having a pathological feature of IDO1 or TDO-mediated tryptophan metabolism.

5. An aza-tryptanthrin derivative represented by Formula (II), or geometric isomers, tautomers, isotopic labelings, hydrates, solvates, metabolites, pharmaceutically acceptable salt or prodrug thereof:

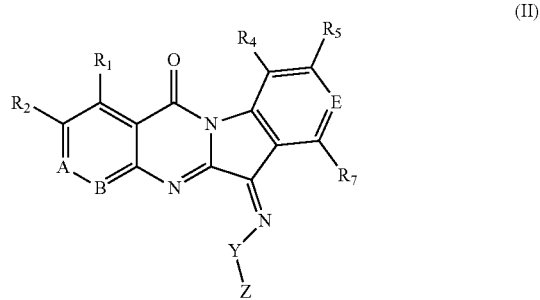

(II)

wherein, in Formula (II)
one of A and B is N, and the other is C—R₃;
E is N or —C—R₆;
Y is —O—, and Z is hydrogen, an unsubstituted or substituted C1-C4 alkyl group, an unsubstituted or substituted C2-C4 alkenyl group, an unsubstituted or substituted C2-C4 alkynyl group, a carboxymethyl group —CH₂C(=O)OH, a sulfonyl group —S(=O)₂OH, or a phosphoryl group —P(=O)(OH)₂; and alternatively, Y is —N(H)—, and Z is hydrogen, —C(=S)—N(R₈)(R₉), —C(=O)—N(R₈)(R₉), or —C(=N)—N(R₈)(R₉);
R₁ to R₇ are each independently selected from hydrogen, an unsubstituted or substituted C1-C4 alkyl group, an unsubstituted or substituted C1-C4 alkoxy group, halogen, a nitro group, a cyano group, a methyl sulfonyl group or a hydroxy group;
R₈ and R₉ are each independently selected from hydrogen or an unsubstituted or substituted C1-C4 alkyl group;
with the provision that when B is N, and A is —CH, and Y is —O—, and Z is hydrogen, and E is —C—R6, R6 is not hydrogen.

6. The derivative of claim 5, wherein A is N, and B is —CH, or B is N and A is —CH.

7. The derivative of claim 5, which is selected from the following compounds:
9-chloro-11-(hydroxyimino)pyrido[2',3':4,5]pyrimido[1,2-α]indol-5(11H)-one;
11-(hydroxyimino)-9-methylpyrido[2',3':4,5]pyrimido[1,2-α]indole-5(11H)-one;
11-(hydroxyimino)-9-methoxypyrido[2',3':4,5]pyrimido[1,2-α]indole-5(11H)-one;
11-((2-(dimethylamino)ethoxy)imino)pyrido[2',3':4,5]pyrimido[1,2-α]indole-5(11H)-one;
11-((2-(dimethylamino)ethoxy)imino)-9-nitropyrido[2',3':4,5]pyrimido[1,2-α]indol-5(11H)-one;
9-chloro-11-((2-(dimethylamino)ethoxy)imino)pyrido[2',3':4,5]pyrimido[1,2-α]indol-5(11H)-one;
11-((2-(dimethylamino)ethoxy)imino)-9-fluoropyrido[2',3':4,5]pyrimido[1,2-α]indol-5(11H)-one;
9-chloro-11-((3-(dimethylamino)propoxy)imino)pyrido[2',3':4,5]pyrimido[1,2-α]indol-5(11H)-one;
11-((2-hydroxyethoxy)imino)-9-nitropyrido[2',3':4,5]pyrimido[1,2-α]indol-5(11H)-one;
N,N-dimethyl-2-(9-nitro-5-oxopyrido[2',3':4,5]pyrimido[1,2-α]indol-11(5H)-ylidene)hydrazine-1-carbothioamide;
2-(9-nitro-5-oxopyrido[2',3':4,5]pyrimido[1,2-α]indol-11(5H)-ylidene)hydrazine-1-carboximidamide;
(((9-methyl-5-oxopyrido[2',3':4,5]pyrimido[1,2-α]indol-11(5H)-ylidene)amino)oxy)sulfonic acid;
11-(methoxyimino)-9-nitropyrido[2',3':4,5]pyrimido[1,2-α]indol-5 (11H)-one;
11-(ethoxyimino)-9-nitropyrido[2',3':4,5]pyrimido[1,2-α]indol-5 (11H)-one;
11-((allyloxy)imino)-9-nitropyrido[2',3':4,5]pyrimido[1,2-α]indol-5(11H)-one;
11-((carboxymethoxyimino)-9-nitropyridine[2',3':4,5]pyrimido[1,2-α]indole-5 (11H)-one;
2-(9-nitro-5-oxopyrido[2',3':4,5]pyrimido[1,2-α]indol-11(5H)-ylidene)hydrazine-1-carbothioamide;
2-(9-methoxy-5-oxopyrido[2',3':4,5]pyrimido[1,2-α]indol-11(5H)-ylidene)-N,N-dimethyl-hydrazine-1-carbothioamide;
2-(9-chloro-5-oxopyrido[2',3':4,5]pyrimido[1,2-α]indol-11(5H)-ylidene)hydrazine-1-carboximidamide;
2-(9-chloro-5-oxopyrido[2',3':4,5]pyrimido[1,2-α]indol-11(5H)-ylidene)hydrazine-1-carbothioamide;
2-(9-(trifluoromethoxy)-5-oxopyrido[2',3':4,5]pyrimido[1,2-α]indol-11(5H)-ylidene)hydrazine-1-carboximidamide;
2-(9-(trifluoromethoxy)-5-oxopyrido[2',3':4,5]pyrimido[1,2-α]indol-11(5H)-ylidene)hydrazine-1-carbothioamide;
2-(9-chloro-5-oxopyrido[3',4':4,5]pyrimido[1,2-α]indol-11(5H)-ylidene)hydrazine-1-carboximidamide; and
2-(9-chloro-5-oxopyrido[3',4':4,5]pyrimido[1,2-α]indol-11(5H)-ylidene)hydrazine-1-carbothioamide.

8. A pharmaceutical composition comprising the derivative as claimed in claim 5.

9. A pharmaceutical composition comprising the derivative as claimed in claim 6.

10. A pharmaceutical composition comprising the derivative as claimed in claim 7.

11. The inhibitor of claim 2, wherein the inhibitor is capable of being used in the treatment of a disease having a pathological feature of IDO1 or TDO-mediated tryptophan metabolism.

12. The inhibitor of claim 3, wherein the inhibitor is capable of being used in the treatment of a diseases having a pathological feature of IDO1 or TDO-mediated tryptophan metabolism.

* * * * *